(12) United States Patent
Hastings et al.

(10) Patent No.: US 8,290,600 B2
(45) Date of Patent: Oct. 16, 2012

(54) ELECTRICAL STIMULATION OF BODY TISSUE USING INTERCONNECTED ELECTRODE ASSEMBLIES

(75) Inventors: Roger Hastings, Maple Grove, MN (US); Martin R. Willard, Burnsville, MN (US); Kevin D. Edmunds, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1043 days.

(21) Appl. No.: 11/490,576

(22) Filed: Jul. 21, 2006

(65) Prior Publication Data

US 2008/0021505 A1      Jan. 24, 2008

(51) Int. Cl.
*A61N 1/00* (2006.01)

(52) U.S. Cl. ............. 607/122; 607/32; 607/33; 607/60; 607/119

(58) Field of Classification Search ............. 607/32–33, 607/60, 122, 119
See application file for complete search history.

(56) References Cited

U.S. PATENT DOCUMENTS

| | | | |
|---|---|---|---|
| 3,057,356 A | 9/1962 | Greatbatch | |
| 3,357,434 A | 12/1967 | Abell | |
| 3,596,662 A | 8/1971 | Bolduc | |
| 3,667,477 A | 6/1972 | Susset et al. | |
| 3,713,449 A | 1/1973 | Mulier | |
| 3,727,616 A | 4/1973 | Lenzkes | |
| 3,835,864 A | 9/1974 | Rasor et al. | |
| 3,902,501 A | 9/1975 | Citron et al. | |
| 3,942,535 A | 3/1976 | Schulman | |
| 3,943,936 A | 3/1976 | Rasor et al. | |
| 4,010,756 A | 3/1977 | DuMont et al. | |
| 4,157,720 A | 6/1979 | Greatbatch | |
| 4,162,679 A | 7/1979 | Reenstierna | |
| 4,198,991 A | 4/1980 | Harris | |
| 4,256,115 A | 3/1981 | Bilitch | |
| 4,441,210 A | 4/1984 | Hochmair et al. | |
| 4,524,774 A | 6/1985 | Hildebrandt | |
| 4,641,664 A | 2/1987 | Botvidsson | |
| 4,644,957 A | 2/1987 | Ricciardelli et al. | |
| 4,681,111 A * | 7/1987 | Silvian .......................... 607/59 | |
| 4,721,118 A | 1/1988 | Harris | |

(Continued)

FOREIGN PATENT DOCUMENTS

EP          1 166 820          1/2002

(Continued)

OTHER PUBLICATIONS

"U.S. Appl. No. 11/316,120, Final Office Action mailed Nov. 12, 2009", 8 pgs.

(Continued)

*Primary Examiner* — Nicole F Lavert
(74) *Attorney, Agent, or Firm* — Schwegman Lundberg & Woessner, P.A.

(57) ABSTRACT

Some embodiments of a cardiac stimulation system may include a plurality of electrode assemblies that are interconnected by one or more wires while at least one of the electrode assemblies (e.g., a control electrode) wirelessly receives energy through inductive coupling with a power communication unit external to the heart (e.g., a device implanted along one or more ribs). These embodiments may provide an arrangement for efficient inductive coupling from the power communication unit to the control electrode. Also, in some circumstances, the cardiac stimulation system may eliminate the need for wired leads that extend to a location outside the heart, thereby reducing the likelihood of infection that passes along the wire and into the heart.

24 Claims, 8 Drawing Sheets

U.S. PATENT DOCUMENTS

| | | |
|---|---|---|
| 4,830,006 A | 5/1989 | Haluska et al. |
| 4,858,623 A | 8/1989 | Bradshaw et al. |
| 4,860,750 A | 8/1989 | Frey et al. |
| 4,953,564 A | 9/1990 | Berthelsen |
| 4,987,897 A | 1/1991 | Funke |
| 5,012,806 A * | 5/1991 | De Bellis ............ 607/33 |
| 5,139,033 A | 8/1992 | Everett et al. |
| 5,143,090 A | 9/1992 | Dutcher et al. |
| 5,170,802 A | 12/1992 | Mehra |
| 5,178,149 A | 1/1993 | Imburgia et al. |
| 5,193,539 A | 3/1993 | Schulman et al. |
| 5,193,540 A | 3/1993 | Schulman et al. |
| 5,234,437 A | 8/1993 | Sepetka |
| 5,250,071 A | 10/1993 | Palermo |
| 5,255,693 A | 10/1993 | Dutcher et al. |
| 5,261,916 A | 11/1993 | Engelson |
| 5,300,107 A | 4/1994 | Stokes et al. |
| 5,304,195 A | 4/1994 | Twyford, Jr. et al. |
| 5,312,415 A | 5/1994 | Palermo |
| 5,312,439 A | 5/1994 | Loeb |
| 5,324,316 A | 6/1994 | Schulman et al. |
| 5,324,325 A | 6/1994 | Moaddeb |
| 5,336,252 A | 8/1994 | Cohen |
| 5,342,408 A * | 8/1994 | deCoriolis et al. ............ 607/32 |
| 5,350,397 A | 9/1994 | Palermo et al. |
| 5,383,915 A * | 1/1995 | Adams ............ 607/60 |
| 5,383,924 A | 1/1995 | Brehier |
| 5,405,367 A | 4/1995 | Schulman et al. |
| 5,411,535 A | 5/1995 | Fujii et al. |
| 5,411,537 A * | 5/1995 | Munshi et al. ............ 607/33 |
| 5,447,533 A | 9/1995 | Vachon et al. |
| 5,487,760 A | 1/1996 | Villafana |
| 5,531,780 A | 7/1996 | Vachon |
| 5,571,148 A | 11/1996 | Loeb et al. |
| 5,622,168 A | 4/1997 | Keusch |
| 5,624,316 A | 4/1997 | Roskowski et al. |
| 5,735,887 A * | 4/1998 | Barreras et al. ............ 607/60 |
| 5,755,764 A | 5/1998 | Schroeppel |
| 5,772,693 A | 6/1998 | Brownlee |
| 5,779,715 A | 7/1998 | Tu |
| 5,800,535 A | 9/1998 | Howard, III |
| 5,814,089 A | 9/1998 | Stokes et al. |
| 5,833,715 A | 11/1998 | Vachon et al. |
| 5,851,227 A | 12/1998 | Spehr |
| 5,871,532 A | 2/1999 | Schroeppel |
| 5,876,429 A | 3/1999 | Schroeppel |
| 5,876,431 A | 3/1999 | Spehr et al. |
| 6,035,239 A | 3/2000 | Patag et al. |
| 6,123,724 A * | 9/2000 | Denker ............ 623/3.11 |
| 6,132,456 A | 10/2000 | Sommer et al. |
| 6,141,588 A | 10/2000 | Cox et al. |
| 6,141,591 A * | 10/2000 | Lenarz et al. ............ 607/57 |
| 6,164,284 A | 12/2000 | Schulman et al. |
| 6,200,303 B1 | 3/2001 | Verrior et al. |
| 6,208,894 B1 | 3/2001 | Schulman et al. |
| 6,223,079 B1 | 4/2001 | Bakels et al. |
| 6,240,316 B1 | 5/2001 | Richmond et al. |
| 6,266,567 B1 | 7/2001 | Ishikawa et al. |
| 6,315,721 B2 | 11/2001 | Schulman et al. |
| 6,345,202 B2 | 2/2002 | Richmond et al. |
| 6,363,938 B2 | 4/2002 | Saadat et al. |
| 6,370,434 B1 | 4/2002 | Zhang et al. |
| 6,381,495 B1 | 4/2002 | Jenkins |
| 6,385,472 B1 | 5/2002 | Hall et al. |
| 6,409,674 B1 | 6/2002 | Brockway et al. |
| 6,442,413 B1 | 8/2002 | Silver |
| 6,445,953 B1 | 9/2002 | Bulkes et al. |
| 6,456,256 B1 | 9/2002 | Amundson et al. |
| 6,501,983 B1 | 12/2002 | Natarajan et al. |
| 6,510,345 B1 * | 1/2003 | Van Bentem ............ 607/60 |
| 6,522,926 B1 | 2/2003 | Kieval et al. |
| 6,556,874 B2 | 4/2003 | Audoglio |
| 6,564,807 B1 | 5/2003 | Schulman et al. |
| 6,574,510 B2 * | 6/2003 | Von Arx et al. ............ 607/60 |
| 6,582,441 B1 | 6/2003 | He et al. |
| 6,589,230 B2 | 7/2003 | Gia et al. |
| 6,614,406 B2 * | 9/2003 | Amundson et al. ............ 343/873 |
| 6,647,291 B1 | 11/2003 | Bonner et al. |
| 6,647,292 B1 | 11/2003 | Bardy et al. |
| 6,783,499 B2 | 8/2004 | Schwartz |
| 6,895,265 B2 | 5/2005 | Silver |
| 6,895,280 B2 | 5/2005 | Meadows et al. |
| 6,907,285 B2 | 6/2005 | Denker et al. |
| 6,917,833 B2 | 7/2005 | Denker et al. |
| 7,003,350 B2 * | 2/2006 | Denker et al. ............ 607/33 |
| 7,006,864 B2 | 2/2006 | Echt et al. |
| 7,050,849 B2 | 5/2006 | Echt et al. |
| 7,076,305 B2 | 7/2006 | Imran et al. |
| 7,184,830 B2 | 2/2007 | Echt et al. |
| 7,209,783 B2 | 4/2007 | Fellows et al. |
| 7,231,260 B2 | 6/2007 | Wallace et al. |
| 7,410,497 B2 | 8/2008 | Hastings et al. |
| 7,522,962 B1 | 4/2009 | Doron et al. |
| 7,532,932 B2 | 5/2009 | Denker et al. |
| 7,532,933 B2 | 5/2009 | Hastings et al. |
| 7,558,631 B2 | 7/2009 | Cowan et al. |
| 7,606,621 B2 | 10/2009 | Brisken et al. |
| 7,610,092 B2 | 10/2009 | Cowan et al. |
| 7,615,010 B1 | 11/2009 | Najafi et al. |
| 7,647,109 B2 | 1/2010 | Hastings et al. |
| 7,650,186 B2 | 1/2010 | Hastings et al. |
| 7,702,392 B2 | 4/2010 | Echt et al. |
| 7,765,001 B2 | 7/2010 | Echt et al. |
| 7,809,438 B2 | 10/2010 | Echt et al. |
| 7,840,281 B2 | 11/2010 | Kveen et al. |
| 7,848,815 B2 | 12/2010 | Brisken et al. |
| 7,848,823 B2 | 12/2010 | Drasler et al. |
| 7,890,173 B2 | 2/2011 | Brisken et al. |
| 7,894,904 B2 | 2/2011 | Cowan et al. |
| 7,894,907 B2 | 2/2011 | Cowan et al. |
| 7,894,910 B2 | 2/2011 | Cowan et al. |
| 7,899,541 B2 | 3/2011 | Cowan et al. |
| 7,899,542 B2 | 3/2011 | Cowan et al. |
| 7,937,161 B2 | 5/2011 | Hastings et al. |
| 7,996,087 B2 | 8/2011 | Cowan et al. |
| 8,050,774 B2 | 11/2011 | Kveen et al. |
| 2001/0018547 A1 | 8/2001 | Mechlenburg et al. |
| 2002/0018379 A1 | 2/2002 | Hakuchoh et al. |
| 2002/0026228 A1 | 2/2002 | Schauerte |
| 2002/0065543 A1 | 5/2002 | Gomperz et al. |
| 2002/0077556 A1 | 6/2002 | Schwartz |
| 2002/0077685 A1 | 6/2002 | Sundquist et al. |
| 2002/0123774 A1 * | 9/2002 | Loeb et al. ............ 607/40 |
| 2002/0123785 A1 | 9/2002 | Zhang et al. |
| 2002/0128546 A1 | 9/2002 | Silver |
| 2002/0138009 A1 | 9/2002 | Brockway et al. |
| 2002/0183791 A1 | 12/2002 | Denker et al. |
| 2002/0188323 A1 | 12/2002 | Penner et al. |
| 2002/0198604 A1 | 12/2002 | Schulman et al. |
| 2003/0036773 A1 | 2/2003 | Whitehurst et al. |
| 2003/0050675 A1 | 3/2003 | Pianca et al. |
| 2003/0074041 A1 | 4/2003 | Parry et al. |
| 2003/0088278 A1 | 5/2003 | Bardy et al. |
| 2003/0109914 A1 | 6/2003 | Westlund et al. |
| 2003/0114735 A1 | 6/2003 | Silver et al. |
| 2003/0158584 A1 | 8/2003 | Cates et al. |
| 2003/0181958 A1 | 9/2003 | Dobak, III |
| 2003/0181959 A1 | 9/2003 | Dobak, III |
| 2003/0204206 A1 | 10/2003 | Padua et al. |
| 2004/0019364 A1 | 1/2004 | Kieval et al. |
| 2004/0059392 A1 | 3/2004 | Parramon et al. |
| 2004/0087831 A1 | 5/2004 | Michels et al. |
| 2004/0098068 A1 | 5/2004 | Carbunaru et al. |
| 2004/0102830 A1 | 5/2004 | Williams |
| 2004/0103906 A1 | 6/2004 | Schulman et al. |
| 2004/0106954 A1 | 6/2004 | Whitehurst et al. |
| 2004/0147973 A1 | 7/2004 | Hauser et al. |
| 2004/0172083 A1 * | 9/2004 | Penner ............ 607/35 |
| 2004/0176672 A1 | 9/2004 | Silver et al. |
| 2004/0176822 A1 * | 9/2004 | Thompson et al. ............ 607/60 |
| 2005/0021108 A1 | 1/2005 | Klosterman et al. |
| 2005/0025797 A1 | 2/2005 | Wang et al. |
| 2005/0043765 A1 | 2/2005 | Williams et al. |
| 2005/0057905 A1 | 3/2005 | He et al. |
| 2005/0096702 A1 | 5/2005 | Denker et al. |
| 2005/0131511 A1 | 6/2005 | Westlund |
| 2005/0182456 A1 | 8/2005 | Ziobro et al. |

| | | | |
|---|---|---|---|
| 2005/0182465 A1 | 8/2005 | Ness | |
| 2005/0251238 A1 | 11/2005 | Wallace et al. | |
| 2005/0251240 A1 | 11/2005 | Doan | |
| 2005/0261741 A1* | 11/2005 | Libbus et al. | 607/3 |
| 2005/0288727 A1 | 12/2005 | Penner | |
| 2006/0015097 A1 | 1/2006 | Mulier et al. | |
| 2006/0020316 A1 | 1/2006 | Martinez et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0095089 A1 | 5/2006 | Soykan et al. | |
| 2006/0136001 A1 | 6/2006 | Ortega et al. | |
| 2006/0136004 A1 | 6/2006 | Cowan et al. | |
| 2006/0173504 A1 | 8/2006 | Zhu et al. | |
| 2006/0173505 A1 | 8/2006 | Salo et al. | |
| 2006/0178719 A1* | 8/2006 | Ideker et al. | 607/119 |
| 2006/0206170 A1 | 9/2006 | Denker et al. | |
| 2007/0075905 A1 | 4/2007 | Denker et al. | |
| 2007/0106357 A1 | 5/2007 | Denker et al. | |
| 2007/0135882 A1 | 6/2007 | Drasler et al. | |
| 2007/0135883 A1 | 6/2007 | Drasler et al. | |
| 2007/0150009 A1 | 6/2007 | Kveen et al. | |
| 2007/0150037 A1 | 6/2007 | Hastings et al. | |
| 2007/0150038 A1 | 6/2007 | Hastings et al. | |
| 2007/0203556 A1 | 8/2007 | Rutten et al. | |
| 2007/0219590 A1 | 9/2007 | Hastings et al. | |
| 2007/0239248 A1 | 10/2007 | Hastings et al. | |
| 2008/0021532 A1 | 1/2008 | Kveen et al. | |
| 2008/0039904 A1 | 2/2008 | Bulkes et al. | |
| 2008/0046040 A1 | 2/2008 | Denker et al. | |
| 2008/0077184 A1 | 3/2008 | Denker et al. | |
| 2008/0077188 A1 | 3/2008 | Denker et al. | |
| 2008/0109054 A1 | 5/2008 | Hastings et al. | |
| 2008/0119911 A1 | 5/2008 | Rosero | |
| 2008/0319502 A1 | 12/2008 | Sunagawa et al. | |
| 2009/0018599 A1 | 1/2009 | Hastings et al. | |
| 2009/0204170 A1 | 8/2009 | Hastings et al. | |
| 2009/0234407 A1 | 9/2009 | Hastings et al. | |
| 2010/0100144 A1* | 4/2010 | Shuros et al. | 607/14 |
| 2010/0314775 A1 | 12/2010 | Schwarzbauer | |
| 2011/0034939 A1 | 2/2011 | Kveen et al. | |
| 2011/0213233 A1 | 9/2011 | Stevenson et al. | |

FOREIGN PATENT DOCUMENTS

| | | |
|---|---|---|
| EP | 1166820 A2 | 1/2002 |
| EP | 1166832 A1 | 1/2002 |
| EP | 1264572 A1 | 12/2002 |
| EP | 0904009 A1 | 9/2003 |
| EP | 1809372 A1 | 7/2007 |
| EP | 1812104 A1 | 8/2007 |
| EP | 1835962 A1 | 9/2007 |
| FR | 2559391 A1 * | 8/1985 |
| JP | 62-254770 A | 6/1987 |
| JP | 02307481 A | 12/1990 |
| JP | 05-076501 | 3/1993 |
| JP | 05076501 A2 | 3/1993 |
| JP | 05245215 | 9/1993 |
| JP | 5245215 | 9/1993 |
| JP | 2005245215 A | 9/1993 |
| JP | 6510459 A | 11/1994 |
| JP | 7016299 A | 1/1995 |
| JP | 9508054 A | 8/1997 |
| JP | 10-509901 | 9/1998 |
| JP | 2000-502931 A | 3/2000 |
| JP | 2001511406 A | 8/2001 |
| JP | 2002510222 A | 4/2002 |
| JP | 2002-514478 A | 5/2002 |
| JP | 2004-173790 A | 6/2004 |
| JP | 2010509901 | 3/2010 |
| NZ | 526115 | 10/2006 |
| NZ | 539770 | 10/2007 |
| NZ | 539771 | 10/2007 |
| WO | WO-9620754 A1 | 7/1996 |
| WO | WO-9725098 A1 | 7/1997 |
| WO | WO-98/26840 A1 | 6/1998 |
| WO | WO-99/06102 A1 | 2/1999 |
| WO | WO-9958191 A1 | 11/1999 |
| WO | WO-00/30534 A1 | 6/2000 |
| WO | WO-01/87137 A2 | 11/2001 |
| WO | WO-03/041793 A2 | 5/2003 |
| WO | WO 03/53491 | 7/2003 |
| WO | WO-03/053491 A1 | 7/2003 |
| WO | WO-03/053491 A2 | 7/2003 |
| WO | WO-03/076010 A1 | 9/2003 |
| WO | WO-03/082403 A2 | 10/2003 |
| WO | WO-2004/002572 A1 | 1/2004 |
| WO | WO-2004012811 A1 | 2/2004 |
| WO | WO-2005/101660 A1 | 10/2005 |
| WO | WO-2006/045073 A1 | 4/2006 |
| WO | WO-2006/045074 A1 | 4/2006 |
| WO | WO 2006/045075 | 4/2006 |
| WO | WO-2006/045075 A1 | 4/2006 |
| WO | WO-2006/096685 A1 | 9/2006 |
| WO | WO-2007/067231 A1 | 6/2007 |
| WO | WO-2007/067253 A1 | 6/2007 |
| WO | WO-2007/078770 A2 | 7/2007 |
| WO | WO-2007/115044 A2 | 10/2007 |
| WO | WO-2008/011626 A1 | 1/2008 |
| WO | WO-2008/034005 A2 | 3/2008 |
| WO | WO-2008/111998 A1 | 9/2008 |

OTHER PUBLICATIONS

"U.S. Appl. No. 11/394,601, Response filed Dec. 2, 2009 to Non Final Office Action mailed Dec. 2, 2009", 11 pgs.

"U.S. Appl. No. 11/490,916, Final Office Action mailed Dec. 17, 2009", 11 pgs.

"U.S. Appl. No. 11/511,152, Non-Final Office Action mailed Dec. 30, 2009", 13 pgs.

"U.S. Appl. No. 11/511,152, Response filed Nov. 12, 2009 to Final Office Action mailed Aug. 10, 2009", 13 pgs.

"U.S. Appl. No. 11/683,577, Final Office Action mailed Nov. 9, 2009", 14 pgs.

"U.S. Appl. No. 11/683,584, Final Office Action mailed Jan. 29, 2010", 9 pgs.

"U.S. Appl. No. 11/745,070, Final Office Action mailed Dec. 11, 2009", 18 pgs.

"U.S. Appl. No. 11/745,105, Response filed Jan. 19, 2010 to Non Final Office Action mailed Sep. 18, 2009", 12 pgs.

"U.S. Appl. No. 11/745,105, Response filed Jun. 22, 2009 to Restriction Requirement mailed May 21, 2009", 6 pgs.

"U.S. Appl. No. 11/745,105, Restriction Requirement mailed May 21, 2009", 6 pgs.

"European Application Serial No. 05815206.7, Communication Dec. 18, 2009", 4 pgs.

"European Application Serial No. 05815215.8, Communication mailed Dec. 18, 2009", 2 pgs.

"European Application Serial No. 05817448.3, Communication mailed Dec. 18, 2009", 2 pgs.

"European Application Serial No. 07759589.0, Office Action mailed Feb. 18, 2010", 3 pgs.

"U.S. Appl. No. 10/971,550, Response to 312 Amendment mailed Apr. 6, 2009", 2 pgs.

"U.S. Appl. No. 11/316,120, Decision on Pre-Appeal Brief mailed Apr. 19, 2011", 2 pgs.

"U.S. Appl. No. 11/316,120, Final Office Action mailed Oct. 28, 2010", 8 pgs.

"U.S. Appl. No. 11/316,120, Notice of Allowance mailed Jul. 20, 2011", 7 pgs.

"U.S. Appl. No. 11/316,120, Pre-Appeal Brief Request filed Mar. 25, 2011", 5 pgs.

"U.S. Appl. No. 11/316,120, Response filed Mar. 25, 2011 to Final Office Action mailed Oct. 28, 2010", 8 pgs.

"U.S. Appl. No. 11/316,120, Supplemental Notice of Allowance mailed Sep. 1, 2011", 4 pgs.

"U.S. Appl. No. 11/394,601, Decision on Pre-Appeal Brief Request mailed Oct. 6, 2010", 2 pgs.

"U.S. Appl. No. 11/394,601, Notice of Allowance mailed Dec. 28, 2010", 8 pgs.

"U.S. Appl. No. 11/490,576, Decision on Pre-Appeal Brief Request mailed Aug. 30, 2011", 2 pgs.

"U.S. Appl. No. 11/490,916, Supplemental Notice of Allowability mailed Oct. 14, 2010", 2 pgs.

"U.S. Appl. No. 11/745,105, Non Final Office Action mailed Feb. 7, 2012", 12 pgs.
"U.S. Appl. No. 11/745,105, Non Final Office Action mailed May 11, 2011", 13 pgs.
"U.S. Appl. No. 11/745,105, Notice of Allowance mailed Oct. 31, 2011", 5 pgs.
"U.S. Appl. No. 11/745,105, Response filed Sep. 12, 2011 to Non-Final Office Action mailed May 11, 2011", 13 pgs.
"U.S. Appl. No. 12/361,884, Non Final Office Action mailed Oct. 12, 2011", 16 pgs.
"U.S. Appl. No. 12/361,884, Preliminary Amendment filed Jun. 30, 2011", 12 pgs.
"U.S. Appl. No. 12/361,884, Supplemental Preliminary Amendment filed Jul. 27, 2011", 12 pgs.
"U.S. Appl. No. 12/365,428, Non Final Office Action mailed Aug. 31, 2011", 9 pgs.
"U.S. Appl. No. 12/365,428, Notice of Allowance mailed Feb. 22, 2012", 8 pgs.
"U.S. Appl. No. 12/365,428, Response filed Jan. 30, 2012 to Non Final Office Action mailed Aug. 31, 2011", 15 pgs.
"U.S. Appl. No. 12/910,106, Non Final Office Action mailed Apr. 4, 2011", 9 pgs.
"U.S. Appl. No. 12/910,106, Notice of Allowance mailed Jan. 26, 2012", 6 pgs.
"U.S. Appl. No. 12/910,106, Notice of Allowance mailed Oct. 27, 2011", 5 pgs.
"U.S. Appl. No. 12/910,106, Response filed Aug. 2, 2011 to Non-Final Office Action mailed Apr. 4, 2011", 14 pgs.
"European Application Serial No. 05815206.7, Response filed Apr. 19, 2010 to Communication Dec. 18, 2009", 27 pgs.
"European Application Serial No. 05815215.8, Response filed Mar. 19, 2010 to Communication mailed Dec. 18, 2009", 12 pgs.
"European Application Serial No. 05817448.3, Response filed Mar. 19, 2010 to Communication mailed Dec. 18, 2009", 9 pgs.
"European Application Serial No. 07759589.0, Summons to Attend Oral Proceedings mailed May 17, 2011", 3 pgs.
"European Application Serial No. 07759589.0, Written Submission filed Dec. 5, 2011 to Summons to Attend Oral Proceedings dated May 17, 2011", 16 pgs.
"Japanese Application Serial No. 2007-538087, Office Action mailed Apr. 11, 2011", (w/ English Translation), 5 pgs.
"Japanese Application Serial No. 2007-538087, Office Action mailed Oct. 5, 2011", (w/ English Translation), 14 pgs.
"Japanese Application Serial No. 2007-538087, Response filed Mar. 23, 2012 to Office Action mailed Oct. 5, 2011", (w/ English Translation of Claims), 9 pgs.
"Japanese Application Serial No. 2007-538087, Response filed Jun. 27, 2011 to Office Action dated Apr. 11, 2011", (w/ English Translation of Claims), 12 pgs.
"Japanese Application Serial No. 2007-538088, Notice of Final Rejection mailed Dec. 6, 2011", (w/ English Translation), 9 pgs.
"Japanese Application Serial No. 2007-538088, Office Action mailed Jun. 13, 2011", (w/ English Translation), 5 pgs.
"Japanese Application Serial No. 2007-538088, Response filed Mar. 27, 2012 to Final Office Action mailed Dec. 6, 2011", (w/ English Translation of Claims), 11 pgs.
"Japanese Application Serial No. 2007-538088, Response filed Aug. 25, 2011 to Office Action dated Jun. 13, 2011", (w/ English Translation of Amended Claims), 9 pgs.
"Japanese Application Serial No. 2007-538089, Office Action mailed Mar. 3, 2011", (w/ English Translation), 6 pgs.
"Japanese Application Serial No. 2007-538089, Response filed May 25, 2011 to Office Action mailed Mar. 3, 2011", (w/ English Translation of Claims), 8 pgs.
"Japanese Application Serial No. 2008-544324, Office Action mailed Nov. 22, 2011", (w/ English Translation), 5 pgs.
"Japanese Application Serial No. 2008-544324, Office Action Response filed Jan. 27, 2012", (w/ English Translation), 10 pgs.
"Japanese Application Serial No. 2008-544332, Office Action mailed Nov. 29, 2011", (w/ English Translation), 5 pgs.
"Japanese Application Serial No. 2008-544332, Response filed Mar. 19, 2012 to Office Action mailed Nov. 29, 2011", (w/ English Translation of Claims), 9 pgs.
"Energy management, wireless and system solutions for highly integrated implantable devices" Doctoral Thesis by Jordi Parramon I Piella for the Universitat Autonoma de Barcelona, certified Dec. 2001.
"Breakthrough Products Could Put Lesser-Known Firms on the Map", by E. Swain, *MDEA 2004*, pp. 56-58, Apr. 2004.
"Novel Passive Implantable Atrial Defibrillator Using Transcutaneous Radiofrequency Energy Transmission Successfully Cardioverts Atrial Fibrillation" by Manoharan et al., for *Circulation*, pp. 1382-1388, Sep. 16, 2003.
Wagner, "Electrodes, Leads, and Biocompatibility," *Design of Cardiac Pacemakers*, 1993, Chapter 6, pp. 133-160 and TOC.
"U.S. Appl. No. 10/971,550, Examiner Interview Summary mailed Jan. 22, 2008", 4 pgs.
"U.S. Appl. No. 11/075,375, Examiner Interview Summary mailed Jan. 12, 2009", 4 pgs.
"U.S. Appl. No. 11/075,375, Examiner Interview Summary mailed May 1, 2008", 4 pgs.
"U.S. Appl. No. 11/075,375, Notice of Allowance mailed Sep. 4, 2009", 6 pgs.
"U.S. Appl. No. 11/075,376, Examiner Interview Summary mailed Jan. 12, 2009", 4 pgs.
"U.S. Appl. No. 11/075,376, Examiner Interview Summary mailed Apr. 2, 2008", 4 pgs.
"U.S. Appl. No. 11/316,120, Non Final Office Action mailed Apr. 11, 2008", 7 pgs.
"U.S. Appl. No. 11/316,120, Non-Final Office Action mailed May 27, 2010", 8 pgs.
"U.S. Appl. No. 11/316,120, Response filed Apr. 12, 2010 to Final Office Action mailed Nov. 12, 2009", 12 pgs.
"U.S. Appl. No. 11/316,120, Response filed May 14, 2008 to Non Final Office Action mailed Apr. 11, 2008", 12 pgs.
"U.S. Appl. No. 11/316,120, Response filed Aug. 27, 2010 to Non Final Office Action mailed May 27, 2010", 13 pgs.
"U.S. Appl. No. 11/394,601, Final Office Action mailed Mar. 22, 2010", 7 pgs.
"U.S. Appl. No. 11/394,601, Pre-Appeal Brief Request filed Jul. 21, 2010", 5 pgs.
"U.S. Appl. No. 11/490,916, Examiner Interview Summary mailed Apr. 12, 2010", 3 pgs.
"U.S. Appl. No. 11/490,916, Examiner Interview Summary mailed Aug. 19, 2009", 2 pgs.
"U.S. Appl. No. 11/490,916, Notice of Allowance mailed Jul. 9, 2010", 4 pgs.
"U.S. Appl. No. 11/490,916, Response filed Jan. 12, 2009 to Restriction Requirement Dec. 11, 2008", 7 pgs.
"U.S. Appl. No. 11/490,916, Response filed Apr. 15, 2010 to Final Office Action mailed Dec. 17, 2009", 12 pgs.
"U.S. Appl. No. 11/511,152, Notice of Allowance mailed Jul. 28, 2010", 6 pgs.
"U.S. Appl. No. 11/511,152, Preliminary Amendment filed Oct. 17, 2006", 3 pgs.
"U.S. Appl. No. 11/511,152, Response filed Jun. 30, 2010 to Non-Final Office Action mailed Dec. 30, 2009", 12 pgs.
"U.S. Appl. No. 11/549,352, Examiner Interview Summary mailed Jun. 25, 2008", 2 pgs.
"U.S. Appl. No. 11/549,352, Examiner's Answer mailed Nov. 27, 2009 to Appeal Brief filed Sep. 9, 2009", 12 pgs.
"U.S. Appl. No. 11/549,352, Reply Brief filed Jan. 27, 2010", 8 pgs.
"U.S. Appl. No. 11/683,577, Examiner Interview Summary mailed Jul. 7, 2009", 4 pgs.
"U.S. Appl. No. 11/683,577, Response filed May 7, 2010 to Final Office Action mailed Nov. 9, 2009", 14 pgs.
"U.S. Appl. No. 11/683,584, Examiner Interview Summary mailed Jul. 7, 2009", 4 pgs.
"U.S. Appl. No. 11/683,584, Preliminary Amendment filed Mar. 8, 2007", 1 pg.
"U.S. Appl. No. 11/683,584, Response filed Jul. 21, 2010 to Final Office Action mailed Jan. 29, 2010", 12 pgs.
"U.S. Appl. No. 11/745,105, Final Office Action mailed Mar. 30, 2010", 9 pgs.
"U.S. Appl. No. 11/745,105, Response filed Jul. 29, 2010 to Final Office Action mailed Mar. 30, 2010", 12 pgs.
"European Application Serial No. 07759589.0, Office Action Response filed Jun. 24, 2010", 6 pgs.
"U.S. Appl. No. 10/971,550, Amendment Under 37 C.F.R. Sec. 1.312 filed Mar. 20, 2009", 6 pgs.
"U.S. Appl. No. 11/075,375, Amendment and Response filed Jan. 12, 2009 to Non-Final Office Action mailed Aug. 11, 2008", 18 pgs.
"U.S. Appl. No. 11/075,375, Final Office Action mailed Apr. 16, 2009", 10 pgs.

"U.S. Appl. No. 11/075,375, Response filed Jul. 16, 2009 to Final Office Actin mailed Apr. 16, 2009", 13 pgs.
"U.S. Appl. No. 11/075,376, Response filed Jan. 21, 2009 to Non-Final Office Action mailed Aug. 20, 2008", 22 pgs.
"U.S. Appl. No. 11/075,376, Final Office Action mailed Apr. 8, 2009", 17 pgs.
"U.S. Appl. No. 11/075,376, Notice of Allowance mailed Aug. 24, 2009", 6 pgs.
"U.S. Appl. No. 11/075,376, Response filed Jul. 8, 2009 to Final Office Action mailed Apr. 8, 2009", 11 pgs.
"U.S. Appl. No. 11/394,601, Non-Final Office Action mailed Sep. 2, 2009", 6 pgs.
"U.S. Appl. No. 11/394,601, Response filed May 4, 2009 to Restriction Requirement mailed Apr. 2, 2009", 9 pgs.
"U.S. Appl. No. 11/394,601, Restriction Requirement mailed Apr. 2, 2009", 10 pgs.
"U.S. Appl. No. 11/511,152, Non-Final Office Action mailed Dec. 23, 2008", 13 pgs.
"U.S. Appl. No. 11/511,152, Final Office Action mailed Aug. 10, 2009", 13 Pgs.
"U.S. Appl. No. 11/511,152, Response filed Mar. 23, 2009 to Non Final Office Action mailed Dec. 23, 2008", 11 pgs.
"U.S. Appl. No. 11/549,352, Final Office Action mailed Mar. 9, 2009", 10 pgs.
"U.S. Appl. No. 11/549,352, Notice of Panel Decision from Pre-Appeal Brief Review mailed Feb. 2, 2009", 2 pgs.
"U.S. Appl. No. 11/549,352, Pre-Appeal Brief for Review filed Dec. 20, 2008", 5 pgs.
"U.S. Appl. No. 11/549,352, Appeal Brief filed Sep. 9, 2009", 37 pgs.
"U.S. Appl. No. 11/683,577, Non-Final Office Action mailed Mar. 5, 2009", 13 pgs.
"U.S. Appl. No. 11/683,577, Response filed Aug. 5, 2009 to Non-Final Office Action mailed Mar. 5, 2009", 10 pgs.
"U.S. Appl. No. 11/683,584, Non-Final Office Action mailed Apr. 1, 2009", 9 pgs.
"U.S. Appl. No. 11/683,584, Response filed Jul. 1, 2009 to Non Final Office Action mailed Apr. 1, 2009", 7 pgs.
"U.S. Appl. No. 11/745,070, Non Final Office Action mailed Apr. 27, 2009", 11 pgs.
"U.S. Appl. No. 11/745,070, Response filed Jul. 27, 2009 to Non Final Office Action mailed Apr. 27, 2009", 11 pgs.
"U.S. Appl. No. 11/745,105, Non-Final Office Action mailed Sep. 18, 2009", 9 pgs.
"European Application Serial No. 06790023.3, Office Action mailed Mar. 4, 2009", 6 pgs.
"European Application Serial No. 06825988.6, Office Action mailed Mar. 4, 2009", 7 pgs.
"European Application Serial No. 07759589.0, Office Action mailed Jan. 29, 2009", 3 pgs.
"European Application Serial No. 07759589.0, Response filed Jun. 5, 2009 to Office Action mailed Jan. 29, 2009", 6 pgs.
"International Application Serial No. PCT/US2005/037978, International Search Report mailed Jun. 13, 2006", 5 pgs.
"International Application Serial No. PCT/US2005/037978, Written Opinion mailed Jun. 13, 2006", 12 pgs.
"International Application Serial No. PCT/US2009/000693, International Search Report mailed May 8, 2009", 5 pgs.
"International Application Serial No. PCT/US2009/000693, Written Opinion mailed May 8, 2009", 8 pgs.
Busch, M., et al., "On the Heating of Inductively Coupled Resonators (Stents) During MRI Examinations", *Magnetic Resonance in Medicine*, 54, (2005), 775-785.
"U.S. Appl. No. 10/971,550 Response filed Feb. 22, 2007 to Restriction Requirement mailed Jan. 22, 2007", 1 pg.
"U.S. Appl. No. 10/971,550 Restriction Requirement mailed Jan. 22, 2007", 22 pgs.
"U.S. Appl. No. 10/971,550, Non- Final Office Action mailed Mar. 19, 2007", 11 pgs.
"U.S. Appl. No. 10/971,550, Non-Final Office Action mailed Nov. 5, 2007", 19 pgs.
"U.S. Appl. No. 10/971,550, Response Filed Sep. 4, 2007 to Non-Final Office Action mailed Mar. 19, 2007", 15 pgs.
"U.S. Appl. No. 10/971,550 Response filed Mar. 25, 2008 to Non FinaL Office Action mailed Nov. 5, 2007", 17 pgs.
"U.S. Appl. No. 11,075,375 Response filed May 7, 2007 to Restriction Requirement mailed Apr. 10, 2007", 8 pgs.
"U.S. Appl. No. 11,075,375 Restriction Requirement mailed Apr. 10, 2007", 6 pgs.
"U.S. Appl. No. 11,075,375 Response filed May 22, 2008 to Final Office Action mailed Jan. 23, 2008", 16 pgs.
"U.S. Appl. No. 11/075,375 Non-Final Office Action mailed Jun. 8, 2007", 11 pgs.
"U.S. Appl. No. 11/075,375, Response filed Oct. 26, 2007 to Non-Final Office Action mailed Jun. 8, 2007", 10 pgs.
"U.S. Appl. No. 11/075,375 Final Office Action mailed Jan. 23, 2008", 10 pgs.
"U.S. Appl. No. 11/075,375, Non-Final Office Action mailed Aug. 11, 2008", 16 pgs.
"U.S. Appl. No. 11/075,376 Restriction Requirement mailed Apr. 10, 2007", 6 pgs.
"U.S. Appl. No. 11/075,376 Non-Final Office Action Mailed Aug. 20, 2008", 16 pgs.
"U.S. Appl. No. 11/075,376 Non-Final Office. Action mailed Jun. 26, 2007", 9 pgs.
"U.S. Appl. No. 11/075,376 Response filed May 7, 2007 to Restriction Requirement mailed Apr. 10, 2007", 10 pgs.
"U.S. Appl. No. 11/075,376, Response filed Oct. 26, 2007 to Non-Final Office Action mailed Jun. 26, 2007", 14 pgs.
"U.S. Appl. No. 11/075,376 Response filed Jun. 9, 2008 to Final Office Action mailed Jan. 7, 2008", 20 pgs.
"U.S. Appl. No. 11/511,152 Preliminary Amendment filed Oct. 17, 2006", 4 pgs.
"U.S. Appl. No. 11/549,352, Non-Final Office Action mailed Feb. 5, 2008", 11 pgs.
"U.S. Appl. No. 11/549,5352, Response filed Jul. 7, 2008 to Non-Final Office Action mailed Feb. 5, 2008", 17 pgs.
"U.S. Appl. No. 11/971,550 Notice of Allowance mailed Jul. 14, 2008", 4 pgs.
"U.S. Appl. No. 11/075,376 Final Office Action mailed Jan. 7, 2008", 11 pgs.
"U.S. Appl. No. 11/549,352 Final Office Action Mailed on Aug. 26, 2008", 14 pgs.
"Energy management, wireless and system solutions for highly integrated implantable devices", *Doctoral Thesis by Jordi Parramon Piella for the Universitat Autonoma de Barcelona*, certified Dec. 2001, 62 pgs.
"International Application No. PCT/US2006/040291 Search Report mailed Apr. 4, 2007", 5 pgs.
"International Application No. PCT/US2006/040291 Written Opinion mailed Apr. 4, 2007", 9 pgs.
"International Application Serial No. PCT/US2007/078405, International Search Report mailed May 20, 2008", 5 pgs.
"International Application Serial No. PCT/US2007/078405, Written Opinion mailed May 20, 2008", 7 pgs.
"PCT Application No. PCT/US2005/037979, International Search Report mailed Mar. 21, 2006", 4 pgs.
"PCT Application No. PCT/US2005/037979, Written Opinion mailed Mar. 21, 2006", 8 pgs.
"PCT Application No. PCT/US2007/074135, International Search Report mailed Nov. 6, 2007", 4 pgs.
"PCT Application No. PCT/US2007/074135, Written Opinion mailed Nov. 6, 2007", 8 pgs.
"Telemetry Research Transcutaneous Energy Transfer (TET) Technology Summary", *Telemetry Research Ltd.*, www.telemetryresearch.com,(No date listed),1 pg.
Manoharan, G., et al., "Novel passive implantable atrial defibrillator using transcutaneous radiofrequency energy transmission successfully cardioverts atrial fibrillation.", *Circulation*, 108(11), (Sep 16, 2003),1382-1388.
Si, Ping , et al., "A Frequency Control Method for Regulating Wireless Power to Implantable Devices", *IEEE Transactions on Biomedical Circuits and Systems*, 2(1), (Mar. 2008),22-29.
Swain, E., "Breakthrough Products Could Put Lesser-Known Firms on the map", *MDDI* (Apr. 2004), [online]. Retrieved from the Internet: <URL: http://www.devicelink.com/mddi/archive/04/04/006.html>, 6 pgs.

* cited by examiner

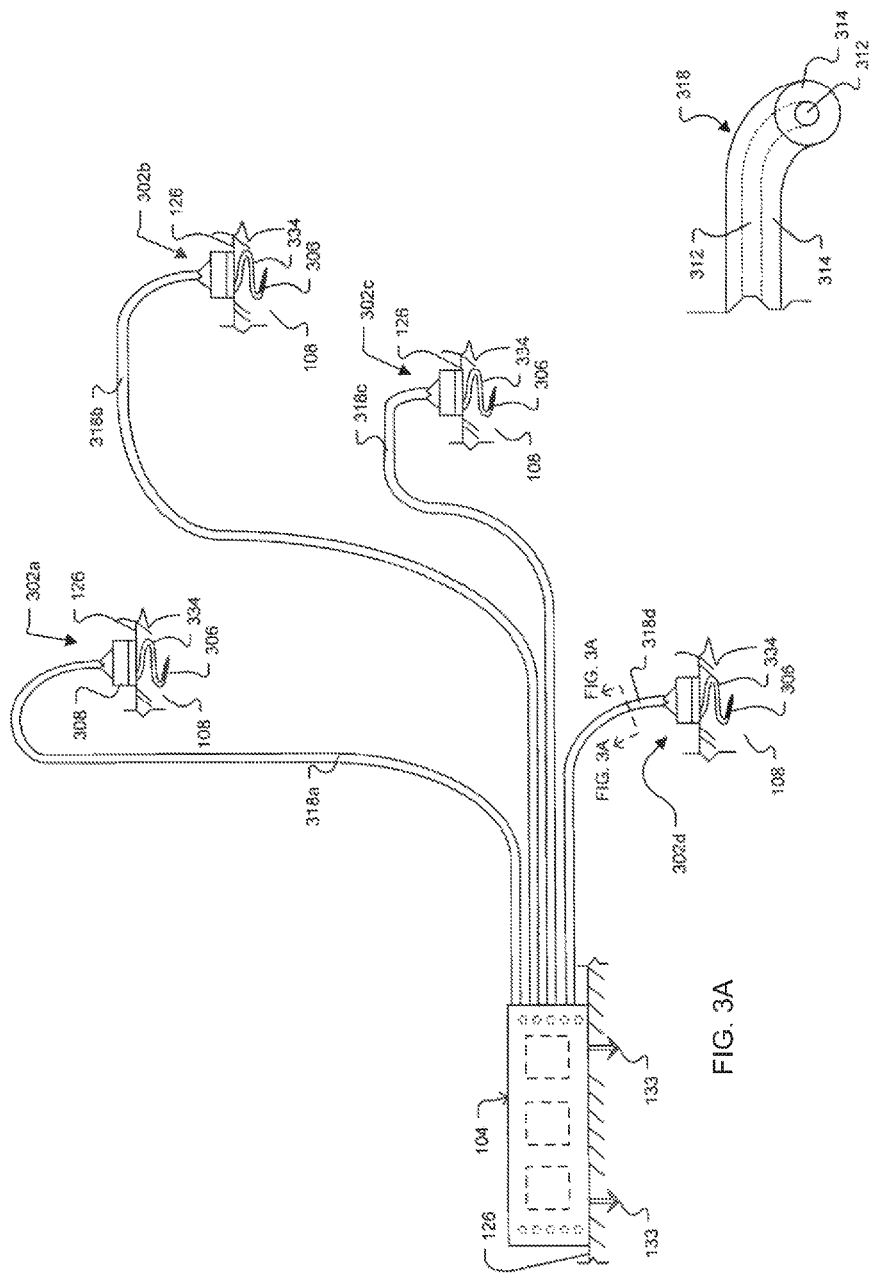

ELECTRICAL STIMULATION OF BODY TISSUE USING INTERCONNECTED ELECTRODE ASSEMBLIES

TECHNICAL FIELD

This document relates to systems that electrically stimulate cardiac or other tissue.

BACKGROUND

Pacing instruments can be used to treat patients suffering from any of a number of heart conditions, such as a reduced ability to deliver sufficient amounts of blood from the heart. For example, some heart conditions may cause or be caused by conduction defects in the heart. These conduction defects may lead to irregular or ineffective heart contractions. Cardiac pacing systems (e.g., a pacemaker or an implantable defibrillator with pacing capability) may be implanted in a patient's body so that wire electrodes in contact with the heart tissue provide electrical stimulation to regulate electrical conduction in the heart tissue. Such regulated electrical stimulation is done to cause the heart to contract and hence pump blood.

The wired pacing systems in current use include a pulse generator that is implanted, typically in a patient's pectoral region just under the skin. One or more wired leads extend from the pulse generator so as to contact various portions of the heart. An electrode at a distal end of a lead may provide the electrical contact to the heart for delivery of the electrical pulses generated by the pulse generator and delivered to the electrode through the lead.

The use of wired leads may limit the number of sites of heart tissue at which electrical energy may be delivered. For example, most commercially available pacing leads are not indicated for use inside the left chambers of the heart. One reason is that the high pumping pressure in the left chambers of the heart may cause a thrombus or clot that forms on the bulky wired lead to eject into distal arteries, thereby causing stroke or other embolic injury. Thus, in order to pace the left side of the heart with a wired lead, most wired leads are directed through the cardiac venous system (outside the left chambers of the heart) to a site in a cardiac vein along the exterior of the left side of the heart.

In one example of a pacing therapy that includes pacing of a left heart chamber, a treatment known as biventricular pacing may be performed when the left ventricle does not contract in synchrony with the right ventricle. In order to perform such pacing therapy, typically a first wired lead is implanted through a vein into the right atrium, a second wired lead is implanted through a vein into the right ventricle, and a third wired lead is implanted through a vein and into the coronary sinus vein (to pace the left ventricle wall from outside the left ventricle). These three wired leads may be connected to a pacemaker device (e.g., implanted in the pectoral region) in an attempt to regulate the contractions of the right and left ventricles.

In addition to conventional wired pacing systems, a new class of pacing system is being developed that includes wireless operation. In such systems, a control module wirelessly communicates with electrode assemblies that are implanted along the outside of the heart tissue or embedded in a cardiac vein. The wireless communication from the control module can provide a source of power through inductive coupling to the implanted electrode assembly. One design issue for such wireless pacing systems is the efficiency of the inductive coupling between the control module and the implanted electrode assemblies, which can impact the battery life of the control module. For example, the further an implanted electrode assembly is away from the control module, the greater the power requirement for the control module to communicate with the implanted electrode. The power draw from the control module battery can be significant when inductively coupling with an implanted electrode assembly disposed on a distant portion of the heart.

SUMMARY

In some embodiments, a system for electrically stimulating heart tissue may include at least one wirelessly powered control assembly that is implantable at least partially in heart tissue. The control assembly may comprise, for example, a conductive coil to wirelessly receive energy from a magnetic field. The system may also include a plurality of stimulation electrode assemblies implantable at least partially into myocardial heart tissue. The system may further include a conductive wire assembly to connect the plurality of stimulation electrode assemblies with the control assembly when the control assembly and the stimulation electrode assemblies are implanted in the heart tissue so that the stimulation electrode assemblies receive electrical energy from the control assembly and deliver electrical stimulation to the heart.

In particular embodiments, a system for electrically stimulating heart tissue may include a wirelessly powered control assembly implantable in heart tissue proximate a heart apex. The control assembly may comprise, for example, an conductive coil to wirelessly receive RF (radio frequency) energy from a RF magnetic field. The system may also include a plurality of stimulation electrode assemblies implantable at least partially into heart tissue. Each stimulation electrode assembly may comprise at least one electrode pole to contact myocardial heart tissue. The system may further include a conductive wire assembly to connect the plurality of stimulation electrode assemblies with the control assembly when the control assembly and the stimulation electrode assemblies are implanted in the heart tissue so that the stimulation electrode assemblies receive electrical energy via the conductive wire assembly and deliver electrical stimulation to the heart. The system may also include a transmitter device implantable in implantable at an implantation site adjacent to one or more ribs and proximate the heart apex, the transmitter device comprising a power source and a RF antenna device to generate the RF magnetic field that wirelessly powers the control assembly.

In some embodiments, a system for electrically stimulating heart tissue may include an implantable stimulation pulse generator component attachable to heart tissue. The stimulation pulse generator component may have a receiver coil to wirelessly receive energy by inductive coupling. The system may also include multiple implantable electrode assemblies to be affixed to heart tissue. Further, the system may include a conductive wire assembly that connects the implantable stimulation pulse generator component with each of the multiple implantable electrode assemblies.

Some or all of the embodiments described herein may have one or more of the following advantages. First, some embodiments of the electrical stimulation system can provide effective cardiac pacing therapy or defibrillation therapy. Second, the stimulation system can provide efficient wireless transmission of power to the components implanted in the heart tissue. Third, such efficient wireless transmission of power to heart-implanted components may reduce the battery requirements, thereby increasing the battery life and possibly providing longer intervals between recharge appointments with a physician (e.g., in those embodiments in which the battery is rechargeable). Fourth, the stimulation electrode assemblies may receive electrical energy via a wire interconnection, but the wire assembly may not extend outside the heart, thereby reducing the likelihood of wire breakage. Fifth, because the wire assembly does not extend to a location outside the heart, the likelihood of an infection migrating into the heart can be reduced.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A is a perspective view of interconnected electrode assemblies, in accordance with some embodiments described herein.

FIG. 3B is a cross-sectional view a portion of the wire assembly shown in FIG. 3A.

Like reference symbols in the various drawings indicate like elements.

DETAILED DESCRIPTION OF ILLUSTRATIVE EMBODIMENTS

Figure 1:
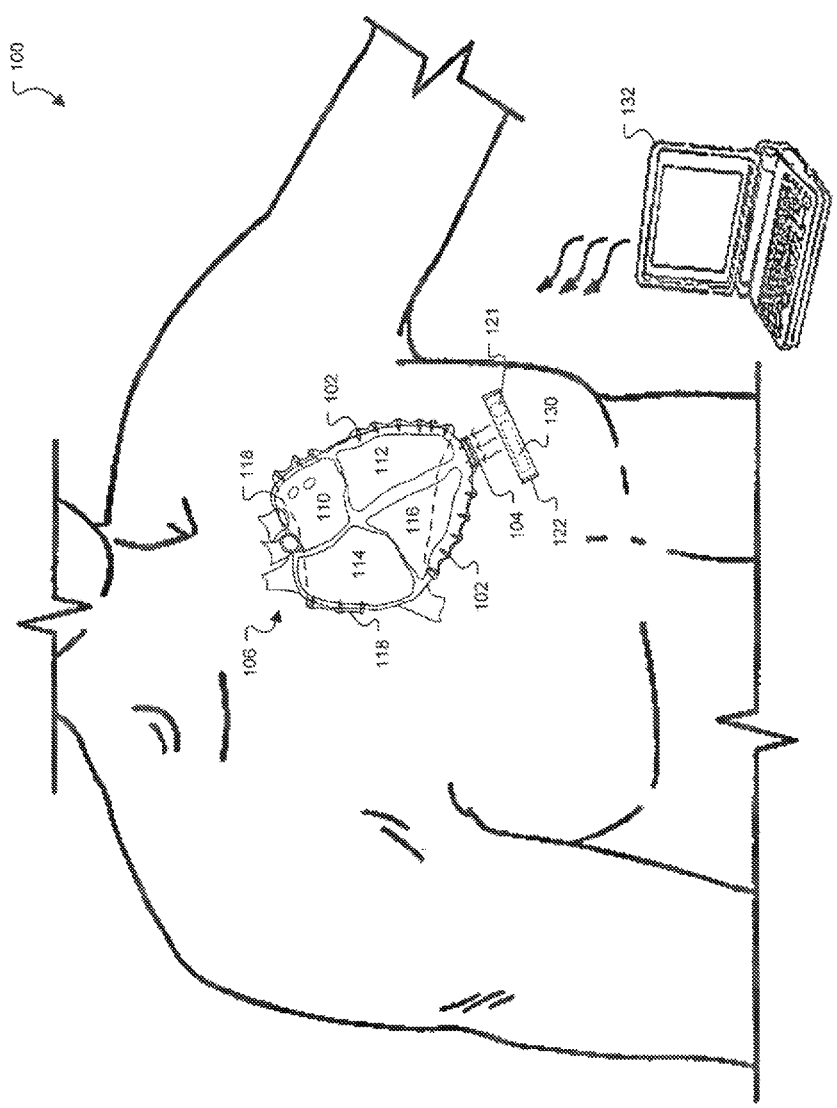
FIG. 1 is a perspective view of a cardiac stimulation system, in accordance with some embodiments described herein.

Referring to FIG. 1, a cardiac stimulation system 100 includes a number of implantable components that can be arranged, for example, within a patient. In this embodiment, the implantable components include a power communication unit 122 that wirelessly transmits radio-frequency (RF) energy or the like, a control electrode assembly 104 that receives the RF energy wirelessly transmitted by the power communication unit 122 (as indicated by the arrows), and a plurality (e.g., seventeen in this example) of stimulation electrode assemblies 102 that are each interconnected with the control electrode assembly 104 by a conductive wire assembly. The wired connection may permit the control electrode assembly 104 to efficiently distribute electrical energy to the stimulation electrode assemblies 102 that are implanted into the heart tissue. As shown in FIG. 1, the system 100 may also include an external device 132 (disposed outside the patient's body) that is capable of communicating wirelessly with the implanted components, for example, with the power communication unit 122.

In the embodiment depicted in FIG. 1, the power communication unit 122 is implanted at a location proximate to the heart 106, for example, between two ribs. This implant location along the ribs, while not used in all embodiments, may be selected due to the close proximity of this location to the control electrode assembly 104 to which the power communication unit 122 wirelessly transmits energy. In these circumstances, maintaining a relatively close distance between the power communication unit 122 and the control electrode assembly 104 helps to reduce battery power requirements for the power communication unit 122 (e.g., the energy draw required to generate a magnetic field may be reduced, thereby providing a longer battery life between recharge appointments, as described in more detail below). It should be understood that, in some embodiments, the power communication unit 122 may be an externally worn device (e.g., worn externally at a location along the one or more ribs).

In some alternative embodiments, the power communication unit 122 may be external to the patient, and may serve to recharge the batteries within the control electrode assembly 104, to deliver physician programming to the software within control electrode assembly 104, or a combination thereof. Such an external power communication unit may reside within a physician's office for patient recharging during routine visits. Alternatively the recharge transmitter and antenna may be incorporated into furniture, incorporated into the patient's bed, or worn by the patient (e.g. in a vest-type garment). In these circumstances, daily recharging for predetermined periods (e.g. 30 minutes) may be preferred to maintain a substantially full charge in the power storage source 123 (e.g., a rechargeable battery or the like) of the control electrode assembly 104.

Figures 2A, 2B:
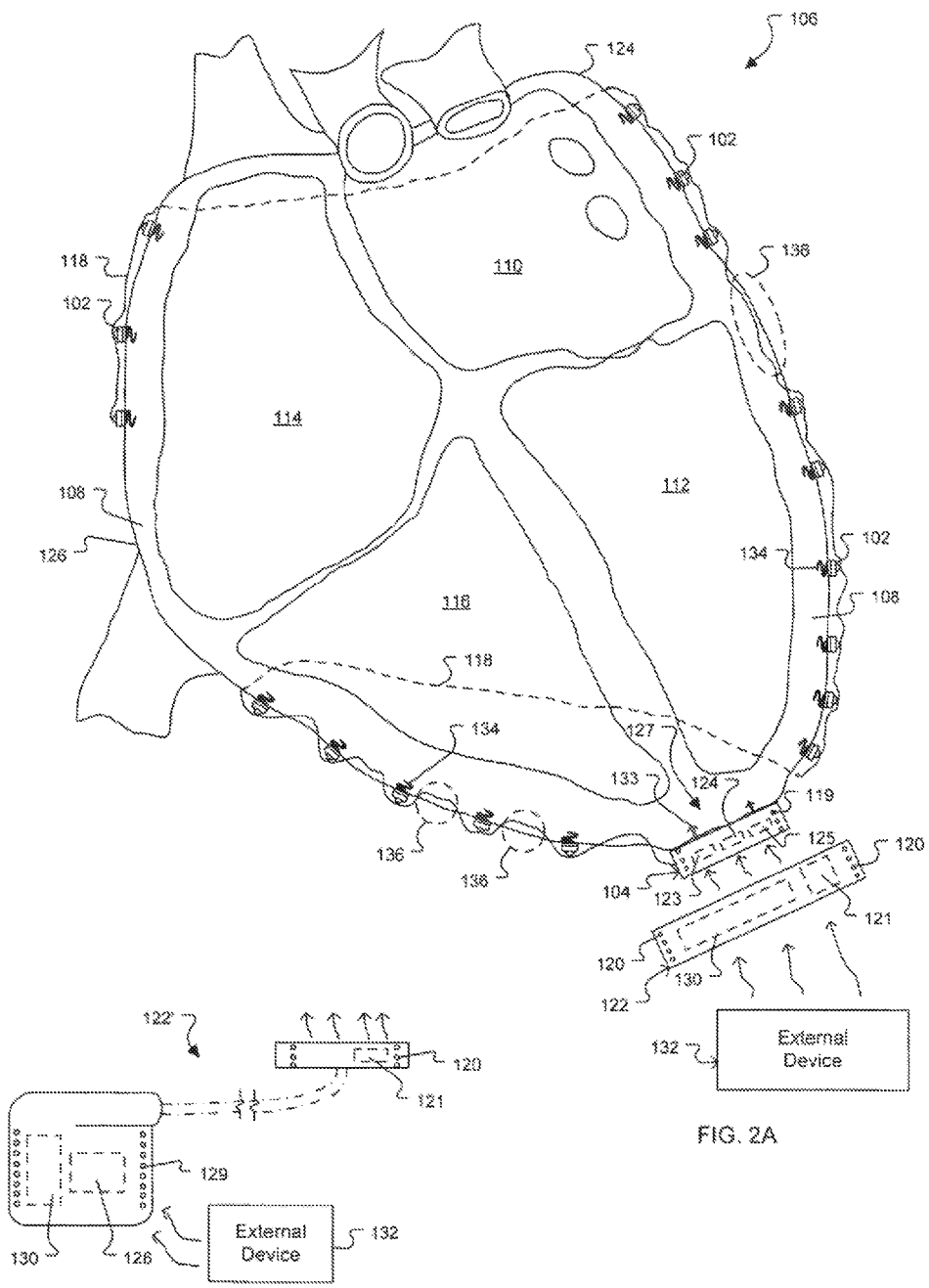
FIG. 2A is perspective view of the cardiac stimulation system of FIG. 1.
FIG. 2B is a partial view of a portion of an alternative embodiment of power communication unit for the cardiac stimulation system of FIG. 1

Referring to FIGS. 1-2A, the control electrode assembly 104 can include a fixation device 133 (described in more detail below) that allows the assembly 104 to be implanted into heart tissue. In the exemplary implant configuration of FIGS. 1-2A, the control electrode assembly 104 is implanted into an external surface of the heart 106 and proximate to the heart's apex 127. This implant location for the control electrode assembly 104, while again not used in all embodiments, may facilitate the relatively close distance between the power communication unit 122 and the control electrode assembly 104, and thus helps to reduce battery power requirements, as previously described. While only one control electrode assembly 104 is implanted in the configuration depicted in FIGS. 1-2A, some embodiments of the system 100 may employ a plurality of control electrode assemblies 104, as described in more detail below.

Each stimulation electrode assembly 102 may also include a fixation device 134 (described in more detail below) that allows the electrode assembly 102 to be implanted into heart tissue. In the embodiment depicted in FIGS. 1-2A, each of the stimulation electrode assemblies 102 is implanted into an external surface of the heart 106, adjacent to one of the four internal heart chambers 110, 112, 114, and 116. In particular, five stimulation electrode assemblies 102 are implanted in the heart wall adjacent to the right ventricle 116, six electrode assemblies 102 are implanted in the heart wall adjacent to the left ventricle 112, and three electrode assemblies 102 are implanted in the heart wall in each of the right and left atria 114 and 110. It should be understood that, in alternative embodiments (described in more detail below in connection with FIG. 10), some or all of the electrode assemblies 102 and 104 can be implanted inside one or more heart chambers 110, 112, 114, and 116 (e.g., implanted through the inner surface of the heart chamber walls).

When electrically activated, the electrode assemblies 102 stimulate the adjacent heart muscle tissue and cause the stimulated heart tissue to contract. In this embodiment, the control electrode assembly 104 is connected to all of the other seventeen electrode assemblies 102 by a conductive wire assembly 118 that extends from the control electrode assembly 104 to each of the seventeen electrode assemblies 102. As previously described, the wired connection may permit the control electrode assembly 104 to efficiently distribute electrical energy to the stimulation electrode assemblies 102 that are implanted adjacent to the heart chambers.

Briefly, in operation, the transmission of RF energy by the power communication unit 122 wirelessly couples (through a shared electromagnetic field) a coil 120 in the unit 122 with a coil 119 in the control electrode assembly 104. The inductive coupling causes an electrical current to be generated within the control electrode assembly 104 that can, for example, charge an internal battery, capacitor, or other rechargeable power source. At an appropriate point in time, the built-up electrical charge may then be selectively delivered, over the conductive wire assembly 118, from the control electrode assembly 104 to any or all of the connected stimulation electrode assemblies 102. The timing of the energy delivery may be controlled, for example, by either the power communication unit 122, the control electrode assembly 104, or the two components in combination, as will be described in more detail below. In some embodiments, the control electrode assembly 104 may itself include a unipolar electrode pole or bipolar electrode poles to stimulate tissue, although such a construction may not used in all embodiments.

The cardiac stimulation system 100 illustrated in FIGS. 1-2A, in some embodiments, can have advantages over other wireless stimulation system designs. For example, the embodiment of the cardiac stimulation system 100 shown in FIGS. 1-2A does not require the wireless transmission of RF energy to each and every stimulation electrode assembly 102 (including a distant electrode assembly 102 implanted adjacent to one of the atria). Instead, in this embodiment, the stimulation electrode assemblies 102 may receive electrical energy from a wired interconnection with a control electrode assembly 104 that is disposed in close proximity to the power communication unit 122. Also, in some embodiments, the stimulation electrode assemblies 102 may have a less complex construction in that each electrode assembly 102 need not have an internal battery or capacitor. Instead, the energy may be stored in the battery, capacitor, or other power source in the control electrode assembly 104, and the charge for a stimulation pulse may be generated only in the control electrode assembly 104 (which selectively delivers the stimulation pulses to the stimulation electrodes 102).

Referring to FIG. 2A, the electrode assemblies 102 and 104 are interconnected to one another by the conductive wire assembly 118 (FIG. 2A). As such, at least one wire may extend along the heart wall between two or more of the electrode assemblies 102 or 104. In the illustrative example shown in FIGS. 1-2A, the wire extends to each stimulation electrode 102 along the outside of the heart 106 (e.g., the dash lines represent the wire extending along the backside of the heart 106). In this embodiment, the conductive wire assembly 118 does not extend outward to another portion of the body (e.g., to a pectoral region for connection with a pacemaker device or the like). Such a configuration can reduce the likelihood of an infection migrating along the wire from another body region and into the heart 106 and may can the likelihood of wire fatigue and breakage. Such beneficial results may be especially enhanced after at least a portion of the wire assembly 118 has been incorporated into the adjacent heart tissue. For example, the wire assembly 118 in this embodiment may be disposed against the epicardial surface 126 of the heart 106 after implantation of the electrode assemblies 102 and 104. In these circumstances, at least a portion of the wire assembly 118 may embed into the adjacent heart tissue 126 over time and may therefore undergo less mechanical stress compared to wire leads that extend to a location outside the heart 106 (e.g., may not be subjected to a substantial number of stress cycles and may therefore be less prone to breakage as a result of the stress cycles).

The wire assembly 118 may comprise at least one wire having a conductive metallic material insulated with a substantially nonconductive material. In some embodiments, the wire may have a fine width, which may further enhance the likelihood of embedding into adjacent heart tissue. For example, the wire may have an outside diameter of less than about 0.010 inches and may be about 0.007 inches in diameter, and the diameter of the conductive metallic material may be less than about 0.008 inches and may be about 0.005 inches in diameter. It is believed that the substantially fine width of the wire 118 facilitates the process over time of the wires 118 incorporating into the heart tissue 136 along the epicardial surface 126 of the heart 106. For example, after the stimulation electrode assembly 102 has been implanted, the wire 118 may be rested against the epicardial surface 126 where the heart tissue may grow over a substantial portion of the wire 118 over a period of time in which the patient heals. When the wire embeds into the adjacent heart tissue, the likelihood of the wire breaking or becoming dislodged is greatly reduced. In some embodiments, the outer surface of the wire may be textured or porous so as to facilitate the embedding process.

Still referring to FIG. 2A, the wire assembly 118 can be used to deliver electrical energy from the control electrode assembly 104 to the stimulation electrode assemblies 102. The electrical energy delivery through the wire assembly 118 may be in the form of electrical stimulation pulses or in the form of a charging current (e.g., to power a charge storage capacitor in each stimulation electrode assembly 102). For example, in the embodiment shown in FIG. 2A, the control electrode assembly 104 includes a power storage source 123 (e.g., a rechargeable battery device, a capacitor, or the like), control circuitry 124, and pulse generator circuitry 125. The electrical stimulation pulses generated by the pulse generator circuitry 125 in the control electrode assembly 104 may be selectively delivered through the wire assembly 118 to the stimulation electrode assemblies 102 for stimulation of the heart chamber walls. In an alternative example, the control electrode assembly 104 may include the power storage source 123 to supply a charging current through the wire assembly 118 to a charge storage capacitor in each stimulation electrode assembly 102. The charging current from the control electrode assembly 104 can be supplied over any time interval in the cardiac cycle, and the control circuitry 124 in the control electrode assembly 104 would selectively signal the stimulation electrode assemblies 102 to activate their charge storage capacitors to provide a local stimulation pulse. Accordingly, in these embodiments, the implanted control electrode assembly 104 may wirelessly receive energy from outside the heart 106 (e.g., from the power communication unit 122) and may deliver electrical energy to other implanted electrode assemblies 102 through the wire assembly 118 for electrical stimulation to the heart 106.

As previously described, the control electrode assembly 104 may include power storage source 123, such as a rechargeable battery, a capacitor, or the like. The power storage source 123 may be wirelessly recharged by the energy received from the inductive coupling between the coil 119 of the control electrode assembly 104 and the coil 120 of the power communication unit 122. For example, a rechargeable battery in the control electrode assembly 104 may be recharged when an RF magnetic field is generated by the power communication unit 122 to wirelessly transmit energy to the coil 119 of the control electrode assembly 104, which is connected to a recharging circuit to deliver a charging current to the battery. In a further example, one or more charge storage capacitors in the control electrode assembly 104 may be recharged when the RF magnetic field is generated by the power communication unit 122. The recharge interval for the power storage source 123 may be affected by the charge volume of the power storage source 123. Additionally, the recharging interval may be affected by the frequency and duration of the stimulation pulses delivered from the stimulation electrode assemblies 102 as required by the patient's heart to maintain a normal rhythm.

Referring to FIG. 2A, in some embodiments, the electrode assemblies 102 and 104 may be implanted through the epicardial tissue 126 of the heart 106 and into the myocardium 108. In some circumstances, the conductive wire assembly 118 and the electrode assemblies 102 and 104 may be disposed fully inside the pericardial space (e.g., the internal space of the pericardium, which is a membranous sac that surrounds the heart 106). The stimulation electrode assemblies 102 and the control electrode assembly 104 may include one or more fixation devices 133 and 134 (e.g., a helical tine, an adjustable hook, or the like) to secure the stimulation electrode assembly 102 to the walls of the heart chambers 110, 112, 114, and 116. In some embodiments, the control electrode assembly 104 may be secured by a fixation device 133 (e.g., retractable tines) proximate the apex 127 of the heart 106—a position that may facilitate efficient inductive coupling with the power communication unit 122. For example, the apex 127 of the heart 106 is generally near the superior surface of the chest and may experience relatively little change in orientation as the heart 106 beats. As such, the control electrode assembly 104 (and the coil 119 therein) does not substantially change orientation relative to the nearby ribs, even when the heart 106 contracts.

The power communication unit 122 may be implanted relatively near the control electrode assembly 104, and in a substantially fixed orientation relative to the control electrode assembly 104. For example, the power communication unit 122 (FIG. 1) may be implanted on, between, or under one or more ribs so as to be located relatively near to the control electrode assembly 104. For example, the coil 120 of the power communication unit 122 may be disposed near the coil 119 of the control electrode assembly at a distance of about 5 mm to about 35 mm, about 5 mm to about 25 mm, and in some embodiments less than about 15 mm. Accordingly, such a substantially stable orientation of the control electrode assembly 104, combined with the generally close proximity between the control electrode assembly 104 and the power communication unit 122, may provide an arrangement for efficient inductive coupling from the power communication unit 122 to the control electrode assembly 104. In such circumstances the power communication unit 122 may readily transmit energy to the power storage device 123 of the control electrode assembly 104 via wireless transmission between the coils 119 and 120.

In the embodiment depicted in FIG. 2A, the power communication unit 122 may comprise a single housing configured to be implanted in proximity to the central electrode assembly 104. The power communication unit 122 may include a power source 130 (e.g., an extended-life battery, a rechargeable battery, one or more capacitors, or the like), the antenna device 121, and the induction coil 120. In those embodiments in which the power source 130 is rechargeable, the energy to recharge the power source 130 may be wireless transmitted (e.g., via an inductive coupling) from an external device 132 located outside the patient's body, such as a recharge unit controlled by a computer device. Because the power communication unit 122 is implanted in a location external to the heart 106 (e.g., along one or more ribs), the power communications unit 122 may include a housing of sufficient size to retain a large-capacity battery. In addition, the efficient inductive coupling between the power communication unit 122 and the control electrode 104 (previously described) may reduce the energy draw from the power source 130 that is used to generate the RF magnetic field. As such, in those embodiments in which the power source 130 comprises a non-rechargeable extended-life battery, the power source may have a lifetime, for example, of more than two years, more than three years, more than four years, and preferably more than six years. Also, in those embodiments in which the power source comprises a rechargeable battery, the power source 130 may have a lifetime after a full charge, for example, of more than one month, more than three months, more than six months, and preferably a year or more. As a result, the recharging of the power source 130 may need only to occur when the patient visits his physician on a monthly, quarterly, or yearly basis.

As previously described, such an extended lifetime of the power source 130 in the power communication unit 122 may be facilitated by the efficient inductive coupling with the control electrode assembly 104. For example, if the power communication unit 122 was required to generate a magnetic field sufficient to individually charge each of the stimulation electrode assemblies 102 (e.g., via an induction coil in each stimulation electrode assembly 102), the energy draw from the power source 130 would be substantial. However, in this embodiment, the power communication unit 122 need only generate a magnetic field to transmit energy to the nearby control electrode assembly 104, which thereafter distributes power to the stimulation electrode assemblies 102 via wire assembly 118. In these circumstances, energy stored in the power source 130 of the power communication unit 122 is drained in a substantially conservative manner, thereby providing a longer lifetime to the power source 130 between recharge appointments.

Referring again to FIGS. 1-2A, the cardiac stimulation system 100 may be used to provide one or more of a number of treatments, such as pacing therapy to regulate the contractions of the heart 106 or defibrillation therapy of the heart 106. During electrical stimulation, a wave of depolarization energy supplied by the stimulation electrode assembly 102 may propagate outwardly from the stimulation electrode assembly 102 to the stimulated volume of cells, thereby causing the heart 106 to contract. Each stimulation electrode assembly 102 may directly capture a certain volume of heart tissue to electrically stimulate, for example, about ten cubic centimeters. Thus implanting a plurality of stimulation electrode assemblies 102 in the heart 106 may provide the stimulation system 100 with the ability to capture a substantial portion of the myocardial tissue around the one or more targeted heart chambers 110, 112, 114, and 116. In theses circumstances, the likelihood of the heart 106 fibrillating or developing an arrhythmia may be substantially reduced.

In one example, consider a left ventricle 112 having an average diameter of about eight centimeters and an average wall thickness of about one centimeter. The total tissue volume of the left ventricle 112 could be estimated at about 200 cubic centimeters. Implanting approximately twenty stimulation electrode assemblies 102 (200 cubic centimeters/10 cubic centimeters/electrode assembly=20 electrode assemblies) that are generally uniformly spaced throughout the left ventricle wall may capture a substantial portion of the myocardial tissue around the left ventricle 112. It should be understood that the estimated number of stimulation electrode assemblies 102 that may be implanted to provide substantially efficient pacing therapy may be dependent upon the size and health of the heart chambers 110, 112, 114, and 116 that will be treated with pacing therapy. In some circumstances, large portions of the heart 106 may be healthy enough so as to provide substantially normal conduction of the depolarization energy wave that may be supplied by the stimulation electrode assembly 102. As a result, fewer stimulation electrode assemblies 102 may be implanted for a given volume of heart tissue while maintaining the complete propagation of the imposed stimulation rhythm. Some patients that will be treated with pacing therapy may receive fewer stimulation electrode assemblies 102, for example, between three and ten stimulation electrode assemblies 102 per heart chamber 110, 112, 114, or 116.

In the embodiments in which the stimulation electrode assemblies 102 can provide pacing therapy, the control electrode assembly 104 (e.g., the control circuitry 124, pulse generator circuitry 125, or a combination thereof) may activate the stimulation electrode assemblies 102 in at least one of a number of different patterns. For example, the control electrode assembly 104 may signal all of the stimulation electrode assemblies 102 disposed in a particular heart chamber to contemporaneously activate, thereby causing that heart chamber to contract (e.g., contemporaneously activate all six of the stimulation electrode assemblies 102 implanted in the myocardial tissue surrounding the left ventricle 112). In these circumstances, all four of the heart chambers 110, 112, 114, and 116 may be contemporaneously contracted (e.g., contemporaneously activating all of the stimulation electrodes 102), or the left and right atria 110 and 114 may be contracted shortly before the left and right ventricles 112 and 116 are contracted. In a second example, the control electrode assembly 104 may signal all of the stimulation electrode assemblies 102 in a particular heart chamber, but the activation of these stimulation electrodes 102 may be offset depending on their location in the tissue around the hearth chamber. In the circumstances in which the stimulation electrode assemblies 102 are positioned around or within an infarct (dead or partially dead) tissue area through which electrical current does not travel or travels relatively slowly, the time differences between activation of the stimulation electrode assemblies 102 may account for the position of the stimulation electrode assemblies 102 and the infarct area. Also, in some circumstances, the stimulation electrode assemblies 102 may be positioned along the propagation path of electrical travel through the heart chamber walls, so the activation of these stimulation electrode assemblies 102 can be offset to mimic the natural electrical travel. In a third example, the control electrode assembly 104 may signal some (or one) but not all of the stimulation electrode assemblies 102 to activate. In some circumstances, not all the of the stimulation electrode assemblies 102 would be needed for effective pacing therapy, so activating only one or a few of the of the stimulation electrode assemblies 102 can conserve the battery power. The other of the stimulation electrode assemblies 102 that are not used for pacing therapy may be implanted for use in other types of therapies, for example, providing pacing therapy in response to a detected premature ventricular contraction (PVC) that indicates the onset of fibrillation or tachycardia.

In some embodiments in which the stimulation electrode assemblies 102 can provide "on-demand" pacing therapy, the control electrode assembly 104 (e.g., the control circuitry 124, pulse generator circuitry 125, or a combination thereof) may activate the stimulation electrode assemblies 102 in response to a irregular heart rhythm. For example, the plurality of stimulation electrode assemblies 102, the control electrode assembly 104, or a combination thereof may be configured to sense and react to an irregular heart rhythm. In such configurations, one or more of the electrode assemblies 102 and 104 may include sensor circuitry (e.g., electrogram sensor circuitry) that detects irregular heart rhythm. If the stimulation electrode assemblies 102, the control electrode assembly 104, or a combination thereof senses or anticipates an irregular rhythm, the control circuitry 124 in the control electrode 104 may include a programmed response to activate the stimulation electrode assemblies 102 in a pattern that may substantially restore a regular rhythm.

Additionally, if the control circuitry 124 in the control electrode 104 (or sensor circuitry located elsewhere in the cardiac stimulation system 100) determines that defibrillation therapy should be implemented, the use of multiple electrode assemblies (e.g., electrode assemblies 102 and 104) implanted in the heart chamber walls may reduce the total energy required to defibrillate the heart 106. Such a reduction in the total electrical energy may be achieved because the electric fields fall off rapidly with distance away from the site of stimulation. For example, to capture the entire heart, some conventional defibrillators must use large input energy to capture tissue far removed from the stimulating electrode. As previously described, in some embodiments, about twenty electrode assemblies 102 could therefore capture a substantial portion of the myocardial tissue around the left ventricle 112—a location where ventricle fibrillation can arise. It is believed that delivery of approximately 100 times the pacing threshold energy to each of the twenty electrode assemblies 102 would require less than one milli-joule of input energy, a small fraction of the total electrical energy delivered by conventional defibrillators. In addition, multi-site defibrillation energy could be delivered to the multiple electrode assemblies 102 in a timed sequence that optimizes the probability of defibrillation. Such a sequence may be determined by analysis of the local ECG signals measured from each electrode assembly 102 during a defibrillation episode. Furthermore, the electrode assemblies 102 may be employed to repress premature electrical stimulations arising in the myocardium that can precipitate fibrillation events. These "hot spots" can be repressed by rapid stimulation with a local electrode assembly 102 to keep such tissue refractory.

Referring briefly to FIG. 2B, in an alternative embodiment of the power communication unit 122' may comprise two housings interconnected by a wire. A first housing is implanted along one or more ribs in proximity to the apex 127 of the heart 106, and a second housing can be implanted in a location (e.g., the abdomen) that is convenient for periodic recharging by the external device 132 (e.g., during a physician appointment). In these embodiments, the first housing may include the antenna device 121 and the coil 120 (e.g. to wirelessly communicate with and transmit energy to the control electrode 104 as previously described). Also, the second housing may include the power source 130, control circuitry 128, and a second coil 129 (e.g., to wirelessly receive energy from an external device for periodic recharging of the power source). A wire may be used to deliver electrical current from the power source 130 (in the second housing) to the antenna device 121 and induction coil 120.

Referring now to FIGS. 3A-B, the stimulation electrode assemblies 102 may be connected to the control electrode assembly 104 by one of a number of wire assemblies. In this embodiment, each stimulation electrode assembly 302a-d (e.g., constructed similar to stimulation electrode assemblies 102 shown in FIG. 2A) may be individually connected to the control electrode assembly 104 by a dedicated wire 318a-d of the wire assembly 318. For example, a stripline of wires 318a-d may extend from the control electrode assembly 104, and the wires 318a-d may be partially separated from the stripline as each wire 318a-d extends toward its respective stimulation electrode assembly 302a-d. The separately attached wires 318a-d in the stripline may allow the control electrode assembly 104 to individually address the stimulation electrode assemblies 302a-d. As previously described, the stimulation electrode assemblies 302a-d and the control electrode assembly 104 may be implanted on the heart 106, for example, through the epicardial surface 126 and within the pericardial space. The stimulation electrode assemblies 302a-d may include one or more fixation devices 334 (e.g., helical tines) to secure the stimulation electrode assemblies 302a-d to the heart tissue. Also, as previously described, the control electrode assembly 104 may include one or more fixation devices 133 (e.g., retractable tines) to secure the control electrode assembly 104 into the heart tissue. For example, the fixation devices 334 and 133 may penetrate through the epicardium 126 and into the myocardium 108.

The wire assembly 318 shown in FIGS. 3A-B may be employed when the stimulation electrode assemblies 302a-d operate as unipolar electrodes. For example, each wire 318a-d may deliver a power signal from the control electrode 104 to its attached stimulation electrode assembly 302a-d so that stimulation energy can be transmitted from unipolar electrode pole 306 of the stimulation electrode assembly 302a-d to a second pole (e.g., on the control electrode assembly 104). For example, the electrode pole 306 of the stimulation electrode assembly 302a may be disposed along an exposed distal end of the helical tine 334 so that the electrode pole 306 is embedded into the heart tissue 108. As shown in FIG. 3B, the wires 318a-d may comprise a conductive metallic material 312 that may be insulated with a substantially nonconductive material 314. Each of the wires 318a-d may join with a mating jack, a crimp mechanism, or the like on the stimulation electrode assemblies 302a-d. Additionally, the stripline of wires 318a-d may be releasably connected to the control electrode assembly 104 by a mating socket or a mating connector. Optionally, the stripline of wires 318a-d may be integrally constructed with the control electrode assembly 104. In this embodiment, the body 308 of the stimulation electrode assembly 302a-d may include a generally non-curved surface that abuts against the tissue surface when the helical tine 334 penetrates into the tissue 108. Thus, the stimulation electrode assemblies 302a-d is delivered into the myocardium tissue 108 using the helical tine or other fixation device 334 while some portion of the body 308 rests against the tissue surface.

Figure 4A:
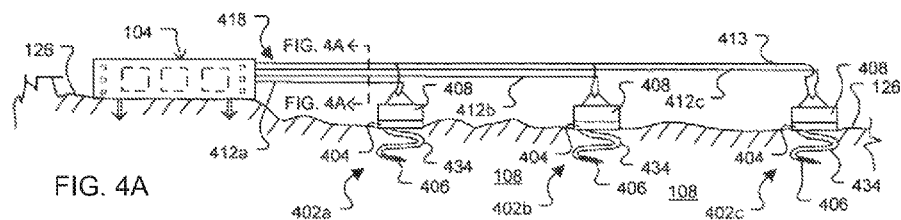
FIG. 4A is a perspective view of another embodiment of interconnected electrode assemblies.
Figure 4B:
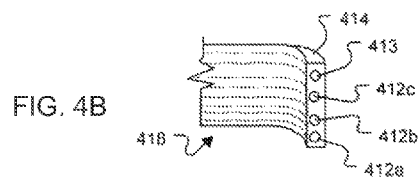
FIG. 4B is a cross-sectional view a portion of the wire assembly shown in FIG. 4A.

Referring now to FIGS. 4A-B, the stimulation electrode assemblies 402a-c may operate as bipolar electrodes and may be connected to the control electrode assembly 104 by a common ground line. In this embodiment a stripline wire assembly 418 having a number of power lines 412a-c and at least one ground line 413 (FIG. 4A) may extend from the control electrode assembly 104. The individual power lines 412a-c may partially separate from the stripline to connect with its associated stimulation electrode assembly 402a-d (e.g., constructed similar to stimulation electrode assemblies 102 shown in FIG. 2A). The ground line 413 in the stripline wire 418 may extend to and connect with all of the stimulation electrode assemblies 402a-d. As shown in FIG. 4B, the lines 412a-c and 413 may comprise a conductive metallic material that is insulated with a substantially nonconductive material 414.

As shown in FIG. 4A, each of the stimulation electrode assemblies 402a-c may contain both a first electrode pole 404 and a second electrode pole 406 that operate as bipolar electrodes. The first electrode pole 404 may be disposed along the portion of the electrode body 408 that presses against or otherwise contacts the heart tissue after implantation, and the second electrode pole 406 may be disposed along an exposed distal end of the helical tine 434 so that the second electrode pole 406 is embedded into the heart tissue 108. As such, stimulation energy can be transmitted between the first and second electrode poles 404 and 406 so as to electrically stimulate the nearby heart tissue (e.g., the myocardial tissue 108 proximate to the electrode assembly 402a-c).

In this embodiment, the control electrode assembly 104 controls the activation of the stimulation electrode assemblies 402a-c in a high side drive mode. That is, the ground line 413 may provide a ground connection from the control electrode assembly 104 to all of the stimulation electrode assemblies 402a-c and the control electrode assembly 104 may individually activate the stimulation electrode assemblies 402a-c by controlling the delivery of electrical energy through each of the separate power line 412a-c, respectively. Because the control electrode 104 is capable of individually transmitting stimulation pulses to selected stimulation electrodes 402a-c, the control electrode 104 may include pulse generator circuitry 125 that generates the stimulation pulses, and the stimulation electrodes 402a-c may have a less complex construction (e.g., no local charge storage capacitors) so as to directly pass the stimulation pulses to the tissue. In an alternate embodiment, the control electrode assembly 104 can control the activation of the stimulation electrode assemblies 402a-c in a low side drive mode. In these circumstances, the electrical line 413 may provide power to all of the stimulation electrode assemblies 402a-c and the control electrode assembly 104 may individually activate the stimulation electrode assemblies 402a-c by controlling the ground connection through the separately connected electrical lines 412a-c.

Figure 5A:
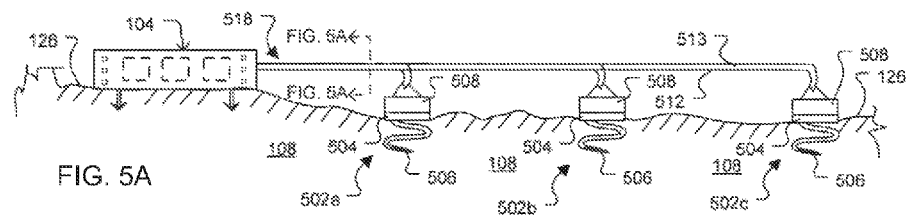
FIG. 5A is a perspective view of another embodiment of interconnected electrode assemblies.
Figure 5B:
FIG. 5B is a cross-sectional view a portion of the wire assembly shown in FIG. 5A.

Referring now to FIGS. 5A-B, some embodiments of the stimulation electrode assemblies may be connected to the control electrode assembly 104 by a wire assembly 518 having a shared power line and a shared ground line. In this embodiment the wire assembly 518 may extend from the control electrode assembly 104 and sequentially connect to a number of stimulation electrode assemblies 502a-c (e.g., constructed similar to stimulation electrode assemblies 102 shown in FIG. 2A). For example, the wire assembly 518 may include a power line 512 that is connected to each of the stimulation electrode assemblies 502a-c and may include a ground line 513 that is connected to each of the stimulation electrode assemblies 502a-c. As shown in FIG. 5B, the wire assembly 518 may comprise a conductive metallic material (to separately form the lines 512 and 513) that may be insulated with a substantially nonconductive material 514. Similar to the embodiments described in connection with FIG. 4A, each of the stimulation electrode assemblies 502a-c may contain both a first electrode pole 504 and a second electrode pole 506 that operate as bipolar electrodes, and the first electrode pole 504 can be disposed along a portion of the electrode body 508. As such, stimulation energy can be transmitted between the first and second electrode poles 504 and 506 so as to electrically stimulate the nearby heart tissue (e.g., the myocardial tissue 108 proximate to the electrode assembly 502a-c). In some circumstances, the one of the electrical lines (e.g., line 513) of the wire assembly 518 may deliver a control signal or other information that causes one of the stimulation electrode assemblies 502a, 502b, or 502c (or a subset of the electrode assemblies 502a-c) to activate and thereby stimulate the nearby heart tissue. In these embodiments, the control electrode 104 may deliver a charging current to charge storage capacitors in the stimulation electrode 502a-c, and the stimulation electrodes 502a-c may have circuitry to detect the activation signal (from the control electrode) and then activate the charge storage capacitor to stimulate the heart tissue.

Figure 6:
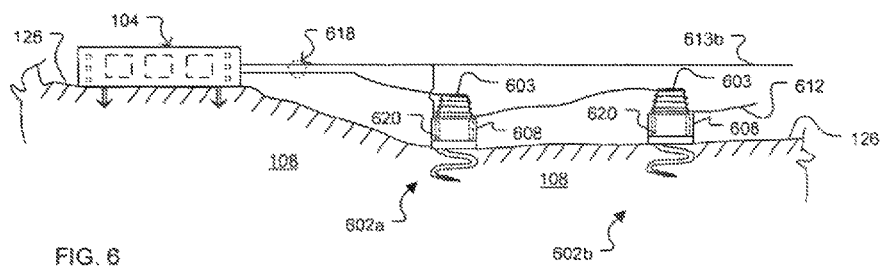
FIG. 6 is a perspective view of another embodiment of electrode assemblies.

Referring to FIG. 6, in some embodiments, the power line 612 of the wire assembly 618 may be connected to one or more stimulation electrode assemblies 602a-b (e.g., constructed similar to stimulation electrode assemblies 102 shown in FIG. 2A) in a manner that inductively transfers the power to the stimulation electrode assemblies 602a-b. In this embodiment, the stimulation electrode assemblies 602a-b may have an attachment post 603 to receive a power line 612 of the wire assembly 618. The power line 612 may be coiled around the attachment post 603 in an orientation to inductively couple with an internal coil 620 of the stimulation electrode assembly 602a-b. Such a connection to the attachment post 603 may facilitate connection of the power line 612 to the electrode body 608. Power may be supplied through the power line 612 at a substantially constant rate or over a particular time interval in the cardiac cycle to charge a power storage device (e.g., rechargeable battery, capacitor, or the like) in each stimulation electrode assembly 602a-b. Optionally, the wire assembly 618 may include a ground line 613 that contacts a ground connection on the electrode assemblies 602a-b. In those embodiments in which the stimulation electrode assemblies 602a-b provide unipolar functionality, the wire assembly 618 may not include the ground line 613.

Figure 7:
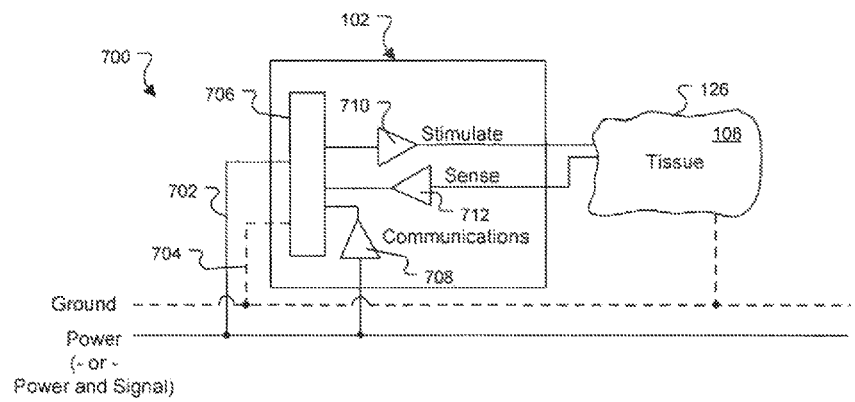
FIG. 7 is a block diagram of a stimulation electrode assembly, in accordance with some embodiments described herein.

Referring to FIG. 7, the each of stimulation electrode assemblies 102 (or stimulation electrode assemblies 302a-d, 402a-c, 502a-c, or 602a-b) may include electrical circuitry 700 contained within the body of the stimulation electrode assembly 102. As previously mentioned above, the stimulation electrode assemblies 102 may receive power signals, control signals, or both from the control electrode assembly 104. At least a power line 702 and optionally a ground line 704 (e.g., in bipolar embodiments) may electrically connect the control electrode assembly 104 (not shown in FIG. 7) with at least a portion of the circuitry 700 (e.g., a microprocessor 706) of the stimulation electrode assembly 102. In some embodiments, communications circuitry 708 (e.g., sense amplifier, address decoder, or the like) may be in electrical communication with the power line 702 (or a separate communication line). In some embodiments, the communications circuitry 708 may be in electrical communication with the microprocessor 706 and may receive a modulated control signal from the control electrode assembly 104, which is demodulated or decoded by the communication circuitry 708 before delivering signal to the microprocessor 706 for subsequent actions. A portion of a modulated signal may comprise coded signals (for example, frequency modulation, amplitude modulation, phase modulation, delta-sigma modulation, or the like). When a given stimulation electrode assembly 102 is activated, a gate (e.g., MOSFET) in the microprocessor 706 may open and the gate may connect the power line 702 to the heart tissue 108 for a pre-determined interval. In an alternative embodiment, the communication circuitry 708 may deliver the modulated control signal to the microprocessor 706, and the microprocessor 706 may perform the demodulation or decoding.

Still referring to FIG. 7, the microprocessor 706 may be in electrical communication with stimulation circuitry 710 (e.g., a charge storage capacitor or the like that can be switched for activation), which is in electrical communication with the heart tissue 108 (e.g., via an electrode pole implanted in or near the myocardial tissue 108). In some embodiments, the microprocessor 706 may provide a gate that permits the stimulation circuitry 710 to receive a charging current. When a control signal from the control electrode assembly 104 is received and interpreted by the microprocessor 706, the microprocessor 706 may switch the stimulation circuitry 710 to an activate mode, and the stimulation circuitry 710 may deliver an electrical stimulation pulse to the heart tissue 108. In other embodiments, the stimulation electrode assemblies 102 may have a less complex configuration that does not include a charge storage capacitor in the stimulation circuitry 710 that is recharged by a charging current transmitted from the control electrode 104. Rather, the control electrode assembly 104 may include pulse generator circuitry 125 and may be connected to the stimulation electrode assemblies 102 in a manner to selectively deliver the stimulation pulses generated within the control electrode 104 (as previously described). In these embodiments, the stimulation circuitry 710 may receive the electrical pulses (e.g., via a dedicated power line) and pass the pulses directly to the heart tissue 108.

In some embodiments, the microprocessor 706 may be in electrical communication with sensor circuitry 712, which is in electrical communication with the heart tissue 108. The sensor circuitry 712 may sense, for example, ECG signals in the heart tissue 108 and deliver signals to the microprocessor 706. In this way, the microprocessor 706 can monitor the heart rhythm on a substantially regular basis. For example, the signal sensed by the sensor circuit 712 may be used by the microprocessor 706 to suspend pacing therapy at that location if a stimulation pulse (e.g., from a heart contraction) has already been sensed, thereby providing on-demand pacing. In another example, the sensed heart rhythm may indicate a fibrillation event, thereby causing the stimulation system 100 to respond with defibrillation therapy. In should be understood, that in some embodiments, the sensed signal information may be communicated back to the control electrode assembly 104 by the power/signal line or a separate communications line (not shown in FIG. 7).

Figure 8:
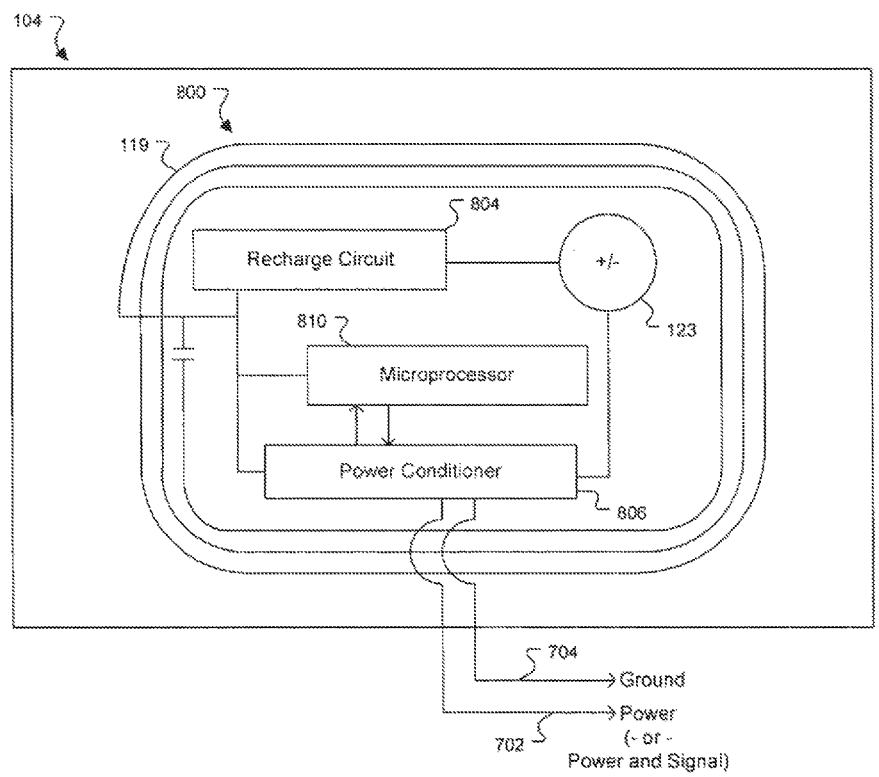
FIG. 8 is a block diagram of an implantable control electrode assembly, in accordance with some embodiments described herein.

Referring to FIG. 8, the control electrode assembly 104 may include electrical circuitry 800 that includes the power storage source 123 (e.g., rechargeable battery, a capacitor, or the like) as previously described in connection with FIGS. 1-2. The power storage source 123 may be in electrical communication with recharge circuitry 804 and power conditioner circuitry 806. As previously described in connection with FIG. 2, the inductive coil 119 may wirelessly receive energy (via inductive coupling with the power communication unit 122) and deliver the energy to the recharge circuitry 804, which uses the energy to recharge the power storage source 123. The coil 119 may also receive information, for example, concerning pulse waveforms, the timing of firing at each stimulation electrode assembly, or the like. In some embodiments, the coil 119 may be used to transmit information related to, for example, the pacing or stimulation thresholds, the sensed electrograms, or the like to the power communication unit 122 or the external device 132.

A microprocessor 810 may be in electrical communication with the power conditioner circuitry 806 so as to coordinate the delivery of the power signal, control signals, ground line, or a combination thereof to the stimulation electrode assemblies 102. For example, as previously described in connection with FIG. 7, the control electrode assembly 104 may provide power signals, control signals, or a combination thereof via a power line 702 while a ground line 704 extends to the stimulation electrode assemblies 102. In some embodiments, the microprocessor 810 may receive, for example, a heart rhythm signal from one or more of the stimulation electrode assemblies 102, thereby permitting the control electrode assembly 104 to monitor the heart rhythms on a substantially regular basis and respond, for example, when irregular heart rhythms are detected.

Figure 9:
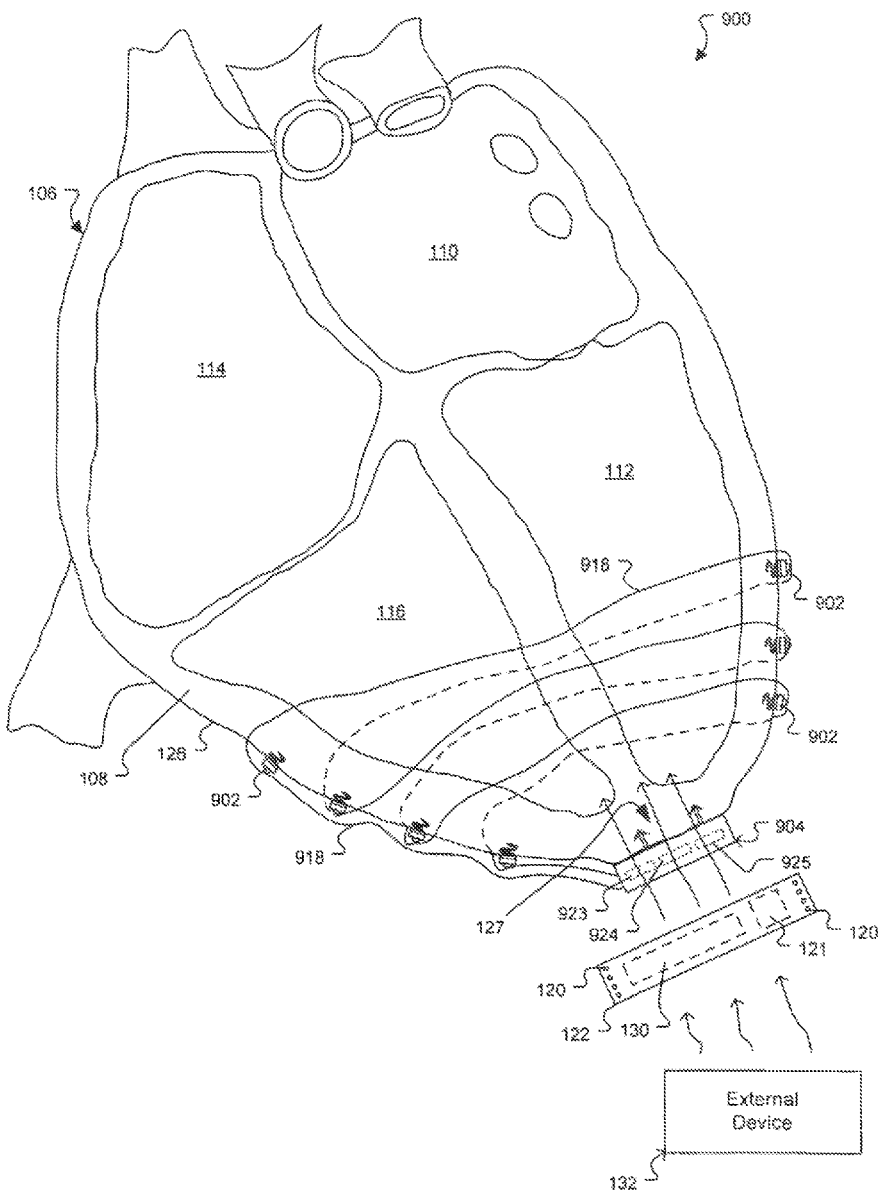
FIG. 9 is a perspective view of another embodiment of a cardiac stimulation system.

Referring to FIG. 9, some embodiments of a cardiac stimulation system may use the wire assembly 918 to contemporaneously serve as an induction coil (e.g., a larger form of the coil 119 described in connection with FIG. 2A). Similar to the previously described embodiments, the cardiac stimulation system 900 may include a plurality of stimulation electrode assemblies 902 and at least one control electrode assembly 904 that are interconnected by a wire assembly 918. The plurality of interconnected electrode assemblies 902 and 904 may be implanted on an outside wall surface of one or more heart chambers 110, 112, 114, and 116. For example, as shown in FIG. 9, one or more stimulation electrode assemblies 902 may be implanted along the outer wall surfaces (e.g., epicardial surfaces) of the left atrium 110, the left ventricle 112, the right atrium 114, and the right ventricle 116, and the control electrode assembly 904 may be implanted along the outer surface of the heart 106 proximate to the apex 127 of the heart 106.

In the embodiment depicted in FIG. 9, the wire assembly 918 may form a closed loop that is coiled around at least a portion of the heart 106 as the wire passes from one stimulation electrode 902 to the next. In such circumstances, the closed-loop wire assembly 918 may serve as a large area inductive coil (e.g., a larger form of the coil 119 described in connection with FIG. 2A) that can be inductively coupled to the power communication unit 122. Similar to previously described embodiments, the power communication unit 122 may be implanted or attached to one or more ribs and may include a coil 120 that generates a magnetic field to wirelessly communicate power to the control electrode assembly 904 implanted on the heart 106. Alternatively, the closed-loop wire assembly 918 may serve as a large area inductive coil that can be inductively coupled to an power communication unit external to the patient's body. For example, the recharge transmitter and antenna may be worn by the patient (e.g. in a vest-type garment) so that the antenna coil is wound around the patient's torso and is inductively coupled to the closed-loop wire assembly 918 implanted along the heart wall.

Similar to previously described embodiments, the wire assembly 918 can be used to deliver electrical energy from the control electrode assembly 904 to the stimulation electrode assemblies 902. The electrical energy delivery through the wire assembly 918 may be in the form of electrical stimulation pulses or in the form of a charging current (e.g., to power a charge storage capacitor in each stimulation electrode assembly 902). For example, in the embodiment shown in FIG. 9, the control electrode assembly 904 includes a power storage source 923 (e.g., a rechargeable battery device, a capacitor, or the like), control circuitry 924, and pulse generator circuitry 925. The electrical stimulation pulses generated by the pulse generator circuitry 925 in the control electrode assembly 904 may be selectively delivered through the wire assembly 918 to the stimulation electrode assemblies 102 for stimulation of the heart chamber walls. In an alternative example, the control electrode assembly 904 may include the power storage source 923 to supply a charging current through the wire assembly 918 to a charge storage capacitor in each stimulation electrode assembly 902. The charging current from the control electrode assembly 904 can be supplied over any time interval in the cardiac cycle, and the control circuitry 924 in the control electrode assembly 904 would selectively signal the stimulation electrode assemblies 902 to activate their charge storage capacitors to provide a local stimulation pulse.

Figure 10:
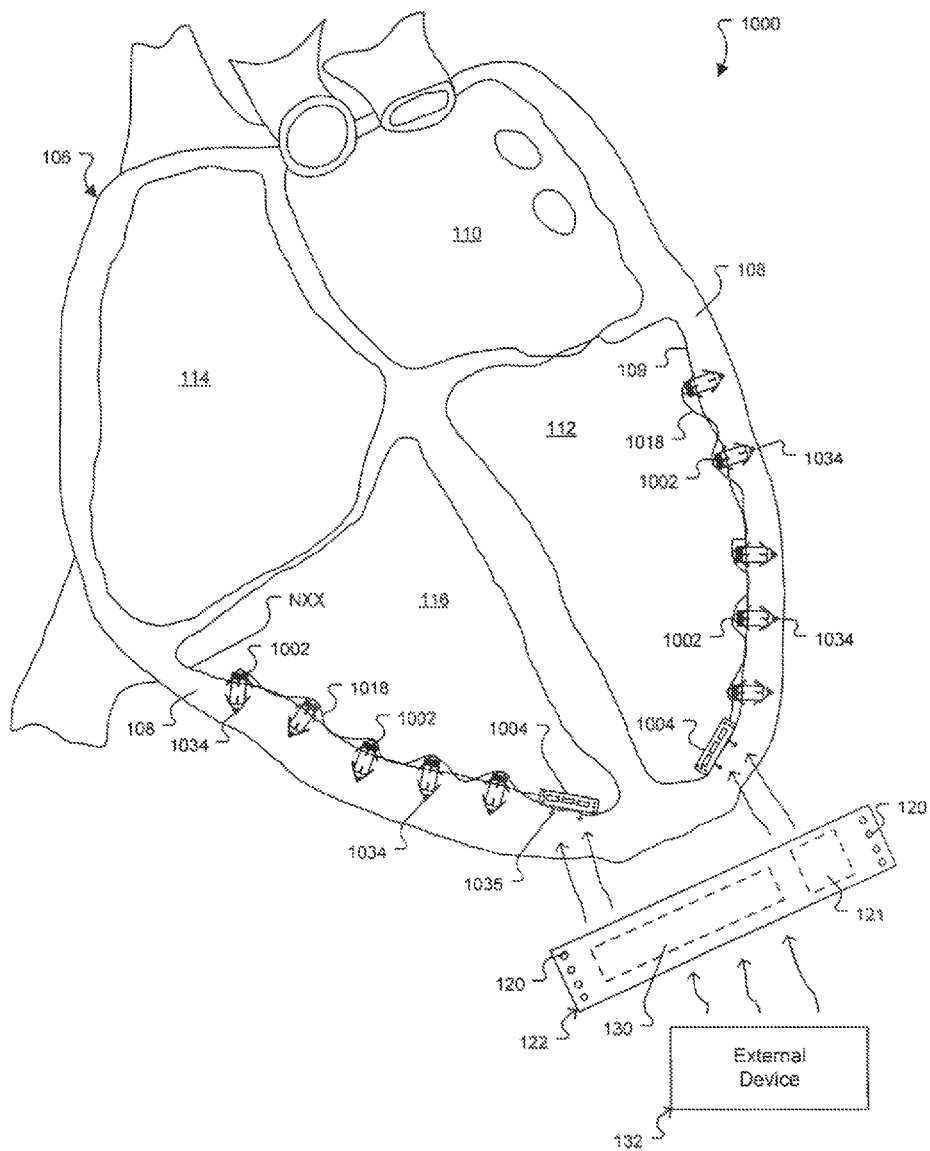
FIG. 10 is a perspective view of another embodiment of a cardiac stimulation system.

Referring to FIG. 10, some embodiments of a cardiac stimulation system 1000 may include stimulation electrode assemblies 1002 (e.g., constructed similar to stimulation electrode assemblies 102 shown in FIG. 2A) and at least one control electrode assembly 1004 (e.g., constructed similar to control electrode assembly 104 shown in FIG. 2A) that are implantable inside one or more heart chambers 110, 112, 114, and 116. For example, in this embodiment one control electrode assembly 1004 is implanted inside the left ventricle 112, and another control electrode assembly 1004 is implanted inside the right ventricle 116. Similar to the embodiments previously described in connection with FIGS. 1-2A, each control electrode assembly 1004 may include a coil that is inductively coupled to the power communication unit 122 so as to receive energy, data, or both, from the power communication unit 122. The two control electrode assemblies 1004 can be disposed proximate to the apex 127 of the heart 106 to provide efficient inductive coupling with the power communication unit 122. A separate wire assembly 1018 may be in electrical communication with each control electrode assembly 1004 and the associated stimulation electrode assemblies 1002 (e.g., those stimulation electrode assemblies 1002 implanted within the same heart chamber). Accordingly, the control electrode assemblies 1004 may wirelessly receive energy from the power communication unit 122 and may transmit energy via a wire assembly to the stimulation electrode assemblies 1002 to thereby stimulate the heart tissue (e.g., myocardial tissue 108).

In this embodiment, the control electrode assemblies 1004 are anchored to the inner wall surface of the left ventricle 112 and the right ventricle 1016 by fixation devices 1035 (e.g., retractable tines or the like). For example, the fixation devices 1035 may penetrate through the endocardium 109 and into the myocardium tissue 108. Also in this embodiment, the stimulation electrode assemblies 1002 are anchored to the inner wall surface of the left ventricle 112 and the right ventricle 116 by fixation devices 1034 (e.g., one or more biased tines near the proximal electrode and one or more opposing biased tines near the distal electrode). For example, the fixation devices 1034 may include biased distal tines that extend outwardly from the body of each electrode assembly 1002 after the distal portion of the body has penetrated through the endocardium 109 and into the myocardium tissue 108. The fixation devices 1034 may also comprise an opposing set of biased proximal tines that extend outwardly from the body of the each electrode assembly 1002. When the opposing biased tines are arranged in such an operative position, the stimulation electrode assembly 1002 remains embedded in the heart chamber wall. Following implantation and a healing period, at least a portion of the stimulation electrode assemblies 1002, the control electrode assembly 1004, and the wire assemblies 1018 may be incorporated into the adjacent heart tissue. In these embodiments, the wire assemblies 1018 do not exit the heart 106, which can reduce the likelihood of an infection migrating from a location outside the heart along a wire and into the heart chambers 110, 112, 114, and 116.

Figure 11A:
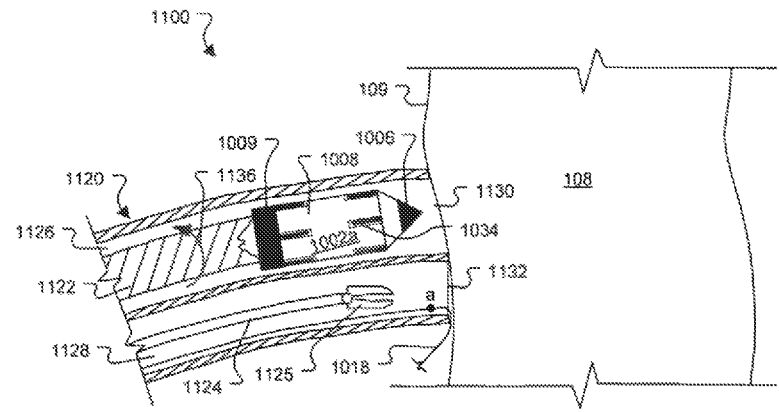
FIGS. 11A-B is a partial cross sectional view of an electrode delivery system, in accordance with some embodiments described herein.
Figure 11B:
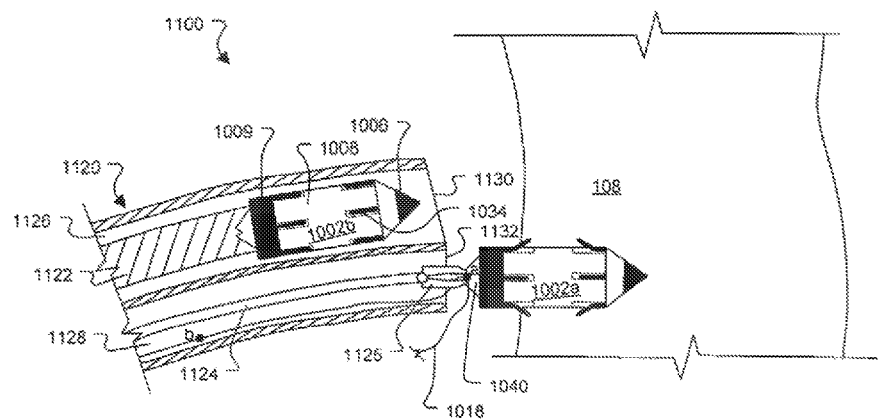

Referring now to FIGS. 11A-B, some embodiments of an electrode assembly delivery system 1100 may be used to implant the stimulation electrode assemblies 1002 (FIG. 10) into the target heart chambers. The sheath system 1100 may include a delivery catheter 1120 that is guided to the targeted heart chamber (e.g., left ventricle 112) via the arterial or venous systems. For example, a steerable guide sheath can be directed through one or more veins to the targeted chamber of the heart 30. After the guide sheath is deployed into the targeted heart chamber, the delivery catheter 1120, which may include a steering mechanism (e.g., steering wires, a shape memory device, or the like) can be advanced through a lumen in the guide sheath to the targeted site on the heart chamber wall. In some circumstances, the guide sheath, the delivery catheter 1120 or both may be directed to the left ventricle 112 by passing through one or more veins, through the right atrium 114, through the atrial septum, through the left atrium 110, and into the left ventricle 112. Preferably, the guide sheath is capable of maintaining a stable valve crossing (e.g., between the left atrium 110 and the left ventricle 112), which can reduce trauma to the valve and facilitate the implantation of multiple stimulation electrode assemblies 1002a into the wall of the targeted heart chamber. In some embodiments, an endoscope or other surgical imaging device may be advanced through the guide sheath of the delivery catheter 1120 to provide the surgeon with images of the surgical site inside the heart chamber. Although FIGS. 11A-B show the delivery of stimulation electrode assemblies 1002a-b, it should be understood from the description herein that, in some embodiments, the delivery catheter 1120 may also be used to deliver the control electrode 1004 (FIG. 10) to the targeted heart chamber.

As shown in FIG. 11A, the stimulation electrode assembly 1002a is shown within a distal portion of the delivery catheter 1120. The stimulation electrode assembly 1002a has a main body 1008 that, in this example, is cylindrically shaped with a conical distal tip portion. The stimulation electrode assembly 1002a may include two bipolar electrodes 1006 and 1009 that are capable of providing an electrical stimulation pulse to nearby heart tissue (e.g., myocardial tissue 108). The distal electrode 1006 is located along the distal end of the stimulation electrode assembly 1002a, and the proximal electrode 1009 is located along a proximal end. As previously described, the stimulation electrode assembly 1002a may include a fixation device in the form of opposing biased tines that are configured to extended outwardly away from the body 1008 when released from the delivery catheter 1120.

In some embodiments, an actuation member 1122 may advance the stimulation electrode assembly 1002a through a first lumen 1126 in the delivery catheter 1120. The actuation member 1122 may releasably engage the stimulation electrode assembly 1002a and may be used to implant the stimulation electrode assembly 1102a into the myocardium 108. For example, the actuation member 1122 may be forced toward the distal end of the delivery catheter 1020 so as to drive the distal electrode 1006 and the biased tines 1034 into the tissue 108. When the biased tines 1034 are separated from the opening at the distal end of the delivery catheter 1020, the biased tines 1034 may shift outwardly away from the electrode body 1008. The actuation member 1122 may continue to be forced toward the distal end of the delivery catheter 1020 so as to drive the proximal electrode 1009 toward the tissue 108. When the biased tines near the proximal electrode 1009 are separated from the opening at the distal end of the delivery catheter 1020, the biased tines may shift outwardly away from the body 1008. In such circumstances, the biased tines 1034 near the distal electrode 1006 may prevent retraction of the wireless electrode assembly 1002a out from the surface of the heart tissue 108. Also, the biased tines near the proximal electrode 1009 may prevent migration of the wireless electrode assembly 1002a through the outside surface of the heart tissue 108. In some embodiments, the opposing biased tines may retain the position of the wireless electrode assembly 1002a so that the tissue 108 may grow and eventually incorporate the wireless electrode assembly 1002a therein, thereby preventing the wireless electrode assembly 1002a from unintentional dislodgement from the tissue 108.

Still referring to FIG. 11A, an wire attachment instrument 1124 may be advanced through a second lumen 1128 of the delivery catheter 1120 to connect the wire 1018 (FIG. 10) to the stimulation electrode 1002a after it is secured to the heart tissue. In this embodiment, the wire attachment instrument 1124 includes an adjustable crimping head 125 at its distal end that is configured to grasp a portion of the wire 1018 extending through the second lumen 1128. The wire 1018 may extend through the second lumen 1128 adjacent to at least a portion of the wire attachment instrument 1124, and a portion of the wire 1018 may extend distally out from the opening 1132 of the second lumen 1128 toward a previously implanted electrode assembly (not shown in FIGS. 11A-B). As described in more detail below, the crimping head 1125 may also direct a portion of the wire 1018 to an implanted electrode assembly 1002a so as to attach that portion of the wire 1018 to the proximal portion of the electrode assembly 1002a. Accordingly, the delivery catheter 1120 may provide access for the implantation of the electrode assemblies 1002a-b and the attachment of the wire interconnections 1018 therebetween.

Referring now to FIG. 11B, after the previously described electrode assembly 1002a has been secured to the heart wall, the delivery catheter may be shifted so that the wire attachment instrument can access the implanted assembly 1002a. The wire attachment instrument 1124 may grasp the wire 1018, for example, at point "a" (shown in both FIGS. 11A and 11B) and direct that portion of the wire 1018 to the connection mechanism 1040 of the electrode assembly 1002a. As previously described, the connection mechanism 1040 may comprising a mating jack, a crimp connector, or the like. The crimping head 1125 of the wire attachment instrument 1124 may crimp or otherwise attach the wire 1018 to the second stimulation electrode assembly 1102a so that the electrode assembly 1002a is connected by the wire 1118 to a previously implanted electrode assembly (not shown in FIGS. 11A-B). After the wire 1018 has been electrically connected to the electrode assembly 1002a, the delivery catheter 1120 may be moved to a subsequent surgical site along the heart chamber wall. As shown, in FIG. 11B, another electrode assembly 1002b may be advanced through the first lumen 1126 of the delivery catheter 1120 in preparation for implantation at the subsequent surgical site. The subsequent electrode assembly 1002b may be implanted into the heart chamber wall using the actuation member 1122 as previously described in connection with FIG. 11A. Thereafter, the wire attachment instrument may grasp another portion of the wire 1018 (e.g., point "b" as shown in FIG. 11B) for connection to the electrode assembly 1002b. Such a delivery procedure may be repeated until the desired number of stimulation electrode assemblies 1002a-b are implanted in the heart chamber and are interconnected by one or more wires 1018 to the control electrode 1004 (FIG. 10). In these circumstances, the power communication unit 122 (FIG. 10) need only generate a magnetic field to transmit energy to the nearby control electrode assemblies 1004 (FIG. 10), which thereafter distributes power to the stimulation electrode assemblies 1002*a*-*b* via the wire interconnections 1018.

A number of embodiments of the invention have been described. Nevertheless, it will be understood that various modifications may be made without departing from the spirit and scope of the invention. Accordingly, other embodiments are within the scope of the following claims.

What is claimed is:

1. A system comprising:
    at least one wirelessly powered control assembly sized and shaped to be capable of delivery via an intravascular route and configured for implant at least partially in heart tissue, the control assembly comprising a conductive coil configured to wirelessly receive magnetically-coupled energy from a magnetic field;
    a plurality of stimulation electrode assemblies sized and shaped to be capable of delivery via an intravascular route and configured for implant at least partially into myocardial heart tissue;
    a conductive wire assembly configured to electrically connect the plurality of stimulation electrode assemblies to the control assembly, the conductive wire assembly configured to be contained entirely within at least one of a heart or a pericardium;
    wherein the control assembly is configured to deliver the received magnetically-coupled energy as electrical stimulation energy to at least one of the plurality of stimulation electrode assemblies using the conductive wire assembly; and
    wherein the stimulation electrode assemblies are configured to receive the electrical stimulation energy from the control assembly using the conductive wire assembly and to deliver the received electrical stimulation energy as an electrical stimulation to the myocardial heart tissue.

2. The system of claim 1, comprising a transmitter sized and shaped to be capable of implant in a location external to the pericardium, the transmitter comprising a power source and an antenna, the transmitter configured to generate the magnetic field using the antenna to provide the magnetically-coupled energy to the control assembly.

3. The system of claim 2, wherein the transmitter comprises a housing that is sized and shaped for implantation at a subcutaneous implantation site near one or more ribs of a patient.

4. The system of claim 3, wherein the wirelessly powered control assembly is configured to wirelessly receive energy from the magnetic field when the wirelessly powered control assembly is implanted in the heart tissue along a heart apex near the subcutaneous implantation site of the transmitter.

5. The system of claim 2, wherein the transmitter comprises a transmitter coil configured to provide an inductive coupling between the transmitter coil and the conductive coil of the wirelessly powered control assembly; and
    wherein the magnetically-coupled energy is transferred from the transmitter coil to the conductive coil using the inductive coupling.

6. The system of claim 5, wherein the transmitter is configured to wirelessly transmit an RF (radio frequency) magnetic field to provide the magnetically-coupled energy to the control assembly.

7. The system of claim 1, wherein the wirelessly powered control assembly comprises at least one pulse generator circuit configured to deliver the received magnetically-coupled energy as one or more electrical stimulation pulses through the conductive wire assembly to one or more of the stimulation electrode assemblies.

8. The system of claim 7, wherein the conductive wire assembly comprises one or more dedicated wire connections for one or more of the stimulation electrode assemblies.

9. The system of claim 8, wherein the wirelessly powered control assembly comprises at least one control circuit configured to selectively deliver the one or more electrical stimulation pulses through the one or more dedicated wire connections.

10. The system of claim 1, wherein one or more of the stimulation electrode assemblies comprises one or more switched capacitors configured to deliver the one or more electrical stimulation pulses to the heart tissue.

11. The system of claim 10, wherein the conductive wire assembly comprises a shared power line and a shared ground line; and
    wherein two or more of the stimulation electrode assemblies are configured to receive the magnetically-coupled energy from the wirelessly powered control assembly using the shared power line and the shared ground line.

12. The system of claim 11, wherein the wirelessly powered control assembly delivers the received magnetically-coupled energy as a charging current to the one or more switched capacitors using at least one of the shared power line or the shared ground line.

13. The system of claim 11, wherein the wirelessly powered control assembly comprises at least one control circuit to selectively deliver one or more activation signals to one or more stimulation electrode assemblies using at least one of the shared power line or the shared ground line, the one or more stimulation electrode assemblies configured to controllably deliver the one or more electrical stimulation pulses in response to receiving a specified activation signal.

14. The system of claim 1, wherein the conductive wire assembly comprises at least one wire having an outside diameter of less than about 0.010 inches.

15. A system comprising:
    a wirelessly powered control assembly sized and shaped to be capable of delivery via an intravascular route and configured for implant at least partially in heart tissue near a heart apex, the control assembly comprising a conductive coil configured to wirelessly receive magnetically-coupled RF (radio frequency) energy from an RF magnetic field;
    a plurality of stimulation electrode assemblies sized and shaped to be capable of delivery via an intravascular route and configured for implant at least partially into myocardial heart tissue, each stimulation electrode assembly comprising at least one electrode pole to contact the myocardial heart tissue;
    a conductive wire assembly configured to electrically connect the plurality of stimulation electrode assemblies to the control assembly, the conductive wire assembly configured to be contained entirely within at least one of a heart or a pericardium;
    a transmitter sized and shaped to be capable of implant at a subcutaneous site near at least one of one or more ribs or the heart apex, the transmitter comprising a power source and an RF antenna, the RF antenna conductively coupled to the power source and the RF antenna configured to generate the RF magnetic field to provide the magnetically-coupled RF energy;
    wherein the control assembly is configured to deliver the received magnetically-coupled RF energy as electrical stimulation energy to at least one of the plurality of stimulation electrode assemblies using the conductive wire assembly; and wherein the stimulation electrode assemblies are configured to receive the electrical stimulation energy from the control assembly via the conductive wire assembly and to deliver the received electrical stimulation energy as an electrical stimulation to the myocardial heart tissue.

16. The system of claim 15, comprising an external recharger configured to recharge the power source of the transmitter.

17. A system comprising:
an implantable stimulation pulse generator sized and shaped to be capable of delivery via an intravascular route and configured for implant at least partially in heart tissue, the stimulation pulse generator including a receiver coil configured to wirelessly receive inductively-coupled energy;
multiple implantable electrode assemblies sized and shaped to be capable of delivery via an intravascular route and configured for implant at least partially in myocardial heart tissue;
a conductive wire assembly configured to electrically connect the implantable stimulation pulse generator with each of the multiple implantable electrode assemblies, the conductive wire assembly configured to be contained entirely within at least one of a heart or a pericardium;
wherein the implantable stimulation pulse generator is configured to deliver the received inductively-coupled energy as electrical stimulation energy to at least one of the multiple implantable electrode assemblies using the conductive wire assembly; and
wherein the multiple implantable electrode assemblies are configured to receive the electrical stimulation energy from the implantable stimulation pulse generator using the conductive wire assembly and to deliver the received electrical stimulation energy as an electrical stimulation to the myocardial heart tissue.

18. The system of claim 17, further comprising a transmitter having a transmitter coil configured to inductively couple with the implantable stimulation pulse generator receiver coil; and
wherein the transmitter coil is configured to generate the inductively-coupled energy to be wirelessly received by the receiver coil.

19. The system of claim 18, wherein the transmitter is sized and shaped for subcutaneous implantation between two ribs of a patient.

20. The system of claim 18, wherein the transmitter is configured to be capable of being worn externally by a patient.

21. The system of claim 17, wherein the implantable stimulation pulse generator comprises one or more switched capacitors configured to provide one or more electrical stimulation pulses to one or more of the multiple implantable electrode assemblies.

22. The system of claim 21, wherein the implantable stimulation pulse generator selectively delivers one or more electrical stimulation pulses to one or more of the multiple electrode assemblies.

23. The system of claim 21, wherein one or more of the multiple electrode assemblies comprises at least one gating circuit configured to selectively inhibit delivery of one or more stimulation pulses received from the implantable stimulation pulse generator to heart tissue in response to a signal from the implantable stimulation pulse generator.

24. The system of claim 17, wherein the stimulation pulse generator is sized and shaped for implant near an external surface of an apex of the heart.

* * * * *